US006925328B2

(12) United States Patent
Foster et al.

(10) Patent No.: US 6,925,328 B2
(45) Date of Patent: Aug. 2, 2005

(54) MRI-COMPATIBLE IMPLANTABLE DEVICE

(75) Inventors: Thomas H. Foster, Rochester, NY (US); Patrick R. Connelly, Rochester, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 322 days.

(21) Appl. No.: 09/921,066

(22) Filed: Aug. 2, 2001

(65) Prior Publication Data

US 2003/0036776 A1 Feb. 20, 2003

Related U.S. Application Data

(63) Continuation-in-part of application No. 09/839,286, filed on Apr. 20, 2001.
(60) Provisional application No. 60/198,631, filed on Apr. 20, 2000.

(51) Int. Cl.$^7$ .................................................. A61N 1/36
(52) U.S. Cl. .............................................. 607/9; 607/2
(58) Field of Search ........................... 607/4, 5, 9, 6, 607/2, 63, 64; 600/411, 413

(56) References Cited

U.S. PATENT DOCUMENTS

| 3,057,356 A | 10/1962 | Greatbatch |
| 3,478,746 A | 11/1969 | Greatbatch |
| 3,508,167 A | 4/1970 | Russell, Jr. |
| 3,669,095 A | 6/1972 | Kobayshi et al. |
| 3,686,958 A | 8/1972 | Porter et al. |
| 3,718,142 A | 2/1973 | Mulier |
| 3,789,667 A | 2/1974 | Porter et al. |
| 3,825,015 A | 7/1974 | Berkovits |
| 4,012,641 A | 3/1977 | Brickerd, Jr. et al. |
| 4,041,954 A | 8/1977 | Ohara |

(Continued)

FOREIGN PATENT DOCUMENTS

WO    WO 01/74241    10/2001

OTHER PUBLICATIONS

A. Jerwzewski et al.:, "Development of an MRI–Compatible Catheter for Pacing the Heart: Initial In Vitro and In Vivo Results," JMRI, ISHRM (US), vol. 6 (No. 6), p. 948–949, (Jun. 14, 1996).
W. Moshage et al., "A Non–Magnetic, MRI Compatible Pacing Center for Clinical Application in Magnetocardiography," Biomedizinixche Technik Band, Erganzungsband (Germany), p. 162–163, (Jun. 14, 1990).
C. Roos, et al., "Fiber Optic Pressure Transducer for Use Near MR Magnetic Fields," RSNA 1985; one page.
K. Wickersheim et al., "Fiberoptic Thermometry and its Applications," J. Microwave Power (1987); pp. 85–94.
Mark B. M. Hofman;"MRI–Compatible Cardiac Pacing Catheter," JMRI: May/Jun. 1997: p. 612.
A.A. Damji et al., "RF Interference Suppression in a Cardiac Synchronization System Operating in High Magnetic Field NMR Imaging System," Magnetic Resonance Imaging, vol. 6, pp 637–640, (1988).

(Continued)

*Primary Examiner*—George R. Evanisko
(74) *Attorney, Agent, or Firm*—Peter J. Mikesell; Howard J. Greenwald

(57) ABSTRACT

A cardiac assist device containing a device for connecting the cardiac assist device to a heart, for furnishing electrical impulses from the cardiac assist device to the heart, for ceasing the furnishing of electrical impulses to the heart, for receiving pulsed radio frequency fields, for transmitting and receiving optical signals, and for protecting the heart and the cardiac assist device from currents induced by the pulsed radio frequency fields. The cardiac assist device contains a control circuit comprised of a parallel resonant frequency circuit.

26 Claims, 12 Drawing Sheets

U.S. PATENT DOCUMENTS

| | | |
|---|---|---|
| 4,050,004 A | 9/1977 | Greatbatch |
| 4,071,032 A | 1/1978 | Schulman |
| 4,091,818 A | 5/1978 | Brownlee et al. |
| 4,200,110 A | 4/1980 | Peterson et al. |
| 4,210,029 A | 7/1980 | Porter |
| 4,254,776 A | 3/1981 | Tanie et al. |
| 4,325,382 A | 4/1982 | Miodownik |
| 4,333,053 A | 6/1982 | Harrison et al. |
| 4,341,221 A | 7/1982 | Testerman |
| 4,379,262 A | 4/1983 | Young |
| 4,432,363 A | 2/1984 | Kakegawa |
| 4,450,408 A | 5/1984 | Tiemann |
| 4,476,870 A | 10/1984 | Peterson et al. |
| 4,491,768 A | 1/1985 | Slicker |
| 4,545,381 A | 10/1985 | Bournay, Jr. et al. |
| 4,611,127 A | 9/1986 | Ibrahim et al. |
| 4,677,471 A | 6/1987 | Takamura et al. |
| 4,686,964 A | 8/1987 | Yunoki et al. |
| 4,691,164 A | 9/1987 | Haragashira |
| 4,719,159 A | 1/1988 | Clark et al. |
| 4,727,874 A | 3/1988 | Bowers et al. |
| 4,763,075 A | 8/1988 | Weigert |
| 4,784,461 A | 11/1988 | Abe et al. |
| 4,798,443 A | 1/1989 | Knipe et al. |
| 4,800,883 A | 1/1989 | Winstrom |
| 4,804,244 A | 2/1989 | Hasegawa et al. |
| 4,827,906 A | 5/1989 | Robicsek et al. |
| 4,827,934 A | 5/1989 | Ekwall |
| 4,858,610 A | 8/1989 | Callaghan et al. |
| 4,879,992 A | 11/1989 | Nishigaki et al. |
| 4,880,004 A | 11/1989 | Baker, Jr. et al. |
| 4,903,701 A | 2/1990 | Moore et al. |
| 4,911,525 A | 3/1990 | Hicks et al. |
| 4,930,521 A | 6/1990 | Metzger et al. |
| 4,934,785 A | 6/1990 | Mathis et al. |
| 4,987,897 A | 1/1991 | Funke |
| 4,991,590 A | 2/1991 | Shi |
| 5,010,888 A | 4/1991 | Jadvar et al. |
| 5,055,810 A | 10/1991 | deLaChapelle et al. |
| 5,058,586 A | 10/1991 | Heinze |
| 5,061,680 A | 10/1991 | Paulson et al. |
| 5,089,697 A | 2/1992 | Prohaska |
| 5,113,859 A | 5/1992 | Funke |
| 5,131,409 A | 7/1992 | Lobarev et al. |
| 5,154,387 A | 10/1992 | Trailer |
| 5,158,932 A | 10/1992 | Hinshaw et al. |
| 5,168,871 A | 12/1992 | Grevious |
| 5,178,149 A | 1/1993 | Imburgia et al. |
| 5,214,730 A | 5/1993 | Nagasawa et al. |
| 5,217,009 A | 6/1993 | Kronberg |
| 5,217,010 A | 6/1993 | Tsitlik et al. |
| 5,226,210 A | 7/1993 | Koskenmaki et al. |
| 5,240,004 A | 8/1993 | Walinsky et al. |
| 5,243,979 A | 9/1993 | Stein et al. |
| 5,265,602 A | 11/1993 | Anderson et al. |
| 5,267,564 A | 12/1993 | Barcel et al. |
| 5,279,292 A * | 1/1994 | Baumann et al. ........... 607/137 |
| 5,324,310 A | 6/1994 | Greeninger et al. |
| 5,330,512 A | 7/1994 | Hauck et al. |
| 5,348,010 A | 9/1994 | Schnall et al. |
| 5,354,220 A | 10/1994 | Ganguly et al. |
| 5,370,668 A | 12/1994 | Shelton |
| 5,387,229 A | 2/1995 | Poore |
| 5,387,232 A | 2/1995 | Trailer |
| 5,402,070 A | 3/1995 | Shelton et al. |
| 5,410,413 A | 4/1995 | Sela |
| 5,415,653 A | 5/1995 | Wardle et al. |
| 5,425,373 A | 6/1995 | Causey, III |
| 5,435,308 A | 7/1995 | Gallup et al. |
| 5,435,316 A | 7/1995 | Kruse |
| 5,438,987 A | 8/1995 | Thacker et al. |
| 5,445,151 A | 8/1995 | Darrow et al. |
| 5,453,838 A | 9/1995 | Danielian et al. |
| 5,454,837 A * | 10/1995 | Lindegren et al. ............. 607/9 |
| 5,456,698 A | 10/1995 | Byland et al. |
| 5,464,014 A | 11/1995 | Sugahara |
| 5,476,095 A | 12/1995 | Schnall et al. |
| 5,520,190 A | 5/1996 | Benedict et al. |
| 5,523,534 A | 6/1996 | Meister et al. |
| 5,569,158 A | 10/1996 | Suzuki et al. |
| 5,570,671 A | 11/1996 | Hickey |
| 5,574,811 A | 11/1996 | Bricheno et al. |
| 5,575,772 A | 11/1996 | Lennox |
| 5,582,170 A | 12/1996 | Soller |
| 5,590,227 A | 12/1996 | Osaka et al. |
| 5,601,611 A | 2/1997 | Fayram et al. |
| 5,603,697 A | 2/1997 | Grundy et al. |
| 5,604,433 A | 2/1997 | Theus et al. |
| 5,611,016 A | 3/1997 | Fangmann et al. |
| 5,619,605 A | 4/1997 | Ueda et al. |
| 5,626,618 A | 5/1997 | Ward et al. |
| 5,626,619 A | 5/1997 | Jacobson et al. |
| 5,631,988 A | 5/1997 | Swirhun et al. |
| 5,634,720 A | 6/1997 | Gallup et al. |
| 5,649,965 A | 7/1997 | Pons et al. |
| 5,653,735 A | 8/1997 | Chen et al. |
| 5,654,317 A | 8/1997 | Fujioka et al. |
| 5,658,966 A | 8/1997 | Tsukamoto et al. |
| 5,679,026 A | 10/1997 | Fain et al. |
| 5,683,435 A | 11/1997 | Truex et al. |
| 5,697,958 A | 12/1997 | Paul et al. |
| 5,699,801 A | 12/1997 | Atalar et al. |
| 5,709,225 A | 1/1998 | Budgifvars et al. |
| 5,716,386 A | 2/1998 | Ward et al. |
| 5,723,856 A | 3/1998 | Yao et al. |
| 5,733,247 A | 3/1998 | Fallon |
| 5,738,105 A | 4/1998 | Kroll |
| 5,749,910 A | 5/1998 | Brumwell et al. |
| 5,752,977 A | 5/1998 | Grevious et al. |
| 5,755,739 A | 5/1998 | Sun et al. |
| 5,755,742 A | 5/1998 | Schuelke et al. |
| 5,759,197 A | 6/1998 | Sawchuk et al. |
| 5,761,354 A | 6/1998 | Kuwano et al. |
| 5,766,227 A | 6/1998 | Nappholz et al. |
| 5,772,604 A | 6/1998 | Langberg et al. |
| 5,774,501 A | 6/1998 | Halpern et al. |
| 5,776,167 A | 7/1998 | Levine et al. |
| 5,776,168 A | 7/1998 | Gunderson |
| 5,782,241 A | 7/1998 | Felblinger et al. |
| 5,782,880 A | 7/1998 | Lahtinen et al. |
| 5,808,730 A | 9/1998 | Danielian et al. |
| 5,814,087 A | 9/1998 | Renirie |
| 5,814,089 A | 9/1998 | Stokes et al. |
| 5,814,090 A | 9/1998 | Latterell et al. |
| 5,814,091 A | 9/1998 | Dahlberg et al. |
| 5,817,130 A | 10/1998 | Cox et al. |
| 5,817,133 A | 10/1998 | Houben |
| 5,817,136 A | 10/1998 | Nappholz et al. |
| 5,818,990 A | 10/1998 | Steijer et al. |
| 5,827,195 A | 10/1998 | Lander |
| 5,827,997 A | 10/1998 | Chung et al. |
| 5,830,209 A | 11/1998 | Savage et al. |
| 5,836,895 A | 11/1998 | Ramsey, III |
| 5,861,012 A | 1/1999 | Stroebel |
| 5,865,839 A | 2/1999 | Doorish |
| 5,867,361 A | 2/1999 | Wolf et al. |
| 5,868,664 A | 2/1999 | Speier et al. |
| 5,869,412 A | 2/1999 | Yenni, Jr. et al. |
| 5,870,272 A | 2/1999 | Seifried et al. |
| 5,871,509 A | 2/1999 | Noren |

| Patent | Date | Inventor |
|---|---|---|
| 5,871,512 A | 2/1999 | Hemming et al. |
| 5,873,898 A | 2/1999 | Hemming et al. |
| 5,882,108 A | 3/1999 | Fraizer |
| 5,882,305 A | 3/1999 | Dumoulin et al. |
| 5,891,171 A | 4/1999 | Wickham |
| 5,895,980 A | 4/1999 | Thompson |
| 5,897,577 A | 4/1999 | Cinbis et al. |
| 5,899,927 A | 5/1999 | Ecker et al. |
| 5,902,326 A | 5/1999 | Lessar et al. |
| 5,916,162 A | 6/1999 | Snelton et al. |
| 5,916,237 A | 6/1999 | Schu |
| 5,917,625 A | 6/1999 | Ogusu et al. |
| 5,919,135 A | 7/1999 | Lemelson |
| 5,928,145 A | 7/1999 | Ocali et al. |
| 5,928,270 A | 7/1999 | Ramsey, III |
| 5,928,570 A | 7/1999 | Reo |
| 5,940,554 A | 8/1999 | Chang et al. |
| 5,946,086 A | 8/1999 | Bruce |
| 5,951,596 A | 9/1999 | Bellinger |
| 5,954,660 A | 9/1999 | Legay et al. |
| 5,957,857 A | 9/1999 | Hartley |
| 5,963,034 A | 10/1999 | Mahapatra et al. |
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. |
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Allred, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | delValle et al. |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley |
| 6,129,745 A | 10/2000 | Sun et al. |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Ken Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |
| 6,216,041 B1 | 4/2001 | Tierney et al. |
| 6,223,083 B1 | 4/2001 | Rosar |
| 6,226,545 B1 | 5/2001 | Gilderdale |
| 6,230,060 B1 | 5/2001 | Mawhinney |
| 6,236,879 B1 | 5/2001 | Konings |
| 6,238,686 B1 | 5/2001 | Burrell et al. |
| 6,240,317 B1 | 5/2001 | Villaseca et al. |
| 6,245,020 B1 | 6/2001 | Moore et al. |
| 6,246,910 B1 | 6/2001 | Bonnet et al. |
| 6,247,474 B1 | 6/2001 | Greeninger et al. |
| 6,254,632 B1 | 7/2001 | Wu et al. |
| 6,256,537 B1 | 7/2001 | Stoop et al. |
| 6,256,541 B1 | 7/2001 | Heil et al. |
| 6,258,087 B1 | 7/2001 | Edwards et al. |
| 6,259,843 B1 | 7/2001 | Kondo |
| 6,259,954 B1 | 7/2001 | Conger et al. |
| 6,263,229 B1 | 7/2001 | Atalar et al. |
| 6,263,242 B1 | 7/2001 | Mika et al. |
| 6,266,555 B1 | 7/2001 | Werner et al. |
| 6,266,563 B1 | 7/2001 | Ken Knight et al. |
| 6,266,564 B1 | 7/2001 | Hill et al. |
| 6,266,566 B1 | 7/2001 | Nichols et al. |
| 6,270,457 B1 | 8/2001 | Bardy |
| 6,270,831 B2 | 8/2001 | Kumar et al. |
| 6,272,377 B1 | 8/2001 | Sweeney et al. |
| 6,272,380 B1 | 8/2001 | Warman et al. |
| 6,274,265 B1 | 8/2001 | Kraska et al. |
| 6,275,730 B1 | 8/2001 | Ken Knight et al. |
| 6,275,732 B1 | 8/2001 | Hsu et al. |
| 6,275,734 B1 | 8/2001 | McClure et al. |
| 6,277,078 B1 | 8/2001 | Porat et al. |
| 6,277,107 B1 | 8/2001 | Lurie et al. |
| 6,278,057 B1 | 8/2001 | Avellanet |
| 6,278,277 B1 | 8/2001 | Zeiger |
| 6,278,894 B1 | 8/2001 | Salo et al. |
| 6,278,897 B1 | 8/2001 | Rutten et al. |
| 6,296,654 B1 | 10/2001 | Ward |
| 6,317,633 B1 | 11/2001 | Jorgenson et al. |
| 6,367,984 B1 | 4/2002 | Stephenson et al. |

OTHER PUBLICATIONS

Frank G. Shellock et al., "Burns Associated with the use of Monitoring Equipment during MR Procedures,"JMRI, Jan./Feb. 1996; pp. 271–272.

J. Nyenhuis et al., "Heating Near Implanted Medical Devices by the MRI RF–Magnetic Field," IEEE Trans. Mag.; Sep. 1999; four pages.

Frank Shellock et al., "Cardiovascular Catheters and Accessories: Ex Vivo Testing of Ferromagnetism, Heating, and Artifacts Associated with MRI," JMRI, Nov./Dec. 1998, vol. 8 #6; pp. 1338–1342.

J. Rod Gimbel et al., "Safe Performance of Magnetic Resonance," PACE; vol. 19; Jun. 1996; pp. 913–919.

National Library of Medicine; "Rapid Ventricular Pacing in a Pacemaker Patient Undergoing Magnetic Resonance Imaging," Pub Med; Pacing Clin Electrophysiol; Jun. 1998; p. 1.

National Library of Medicine;"Effects of Magnetic Resonance Imaging on Cardiac Pacemakers and Electrodes," Pub Med; Am Heart J; (1997); pp. 1–2.

M. Kusumoto et al., "Cardiac Pacing for the Clinician," Lippincott Williams & Wilkins; (2001); Chapter 1, pp. 9, 12, 13, 18, 22, 24.

Donald Fink; "Electronic Engineering," Electronic Engineers Handbook; 2nd edition, Mcgraw Hill; (1982); Section 14; pp. 29–45.

X Luo et al., "Electromagnetic Interference Shielding Using Continuous Carbon–Fiber Carbon–Matrix and Polymer–Matrix Composites," Composites Part B: Engineering; (1999); pp. 227–231.

D.D.L. Chung, "Flexible Graphite for Gasketing, Absorption, Electromagnetic Interference Shielding, Vibration Damping, Electrochemical Applications, and Stress Sensing," Journal of Materials Engineering and Performance; Apr. 2000; vol. 9 p 161–163.

M. Konings et al., "Catheters and Guidewires in Inervential MRI; Problems and Solutions," Medical Mundi; 45/1; Mar. 2001.

M. Konings; "Development of an MR–Safe Tracking Catheter with a Laser DrivenTip Coil," Journal of Magnetic Resonance Imaging 2001:13:131–135. c. 2001 Wiley–Liss, Inc.

Ey Yong et al., "An Optical System for Wireless Detuning of Parallel Resonant Circuits" Journal of Magnetic Resonance Imaging; (2000); vol. 12, pp. 632–638.

Bernd Nowak; "Taking Advantage of Sophisticated Pacemaker Diagnostics," Excerpta Medica; (1999); pp. 172D–179D.

Jose A. Jogler et al., "Interaction of a Commercial Heart Rate Monitor With Implanted Pacemakers," Excerpta Medica; (1999); pp. 790–792.

J.A. Pomposo et al., "Polypyrrole–based Conducting Hot Melt Adhesives for EMI Shielding Applications," Elsevier; Synthetic Metals 104; (1999); pp. 107–111.

K. Grattan et al., "Fiber Optic Sensor Technology: An Overview," Elsevier; Sensors and Actuators 82; (2000);pp. 40–61.

L. Rippert et al., "Optical and Acoustic Damage Detection in Laminated CFRP Composite Materials," Elsevier; Composites Science and Technology 60; (2000); pp. 2713–2724.

C. Strandman et al., "A Production Process of Silicon Sensor Elements for a Fibre–Optic Pressure Sensor,"Elsevier; Sensors and Actuators A63; (1997); pp. 69–74.

D. Howard et al., "A Single–Fringe Etalon Silicon Pressure Transducer," Elsevier; Sensors and Actuators 86; (2000); pp. 21–25.

Dan Haronian, "Displacement Sensing Using Geometrical Modulation in Reflection Mode (GM–RM) of Coupled Optical Waveguides," J. Micromech, Microeng., (UK); (1998); pp. 323–326.

H Ghafour–Shiraz, "A Novel Distributed Feedback Laser Diode Structure foran Optical Wavelength Tunable Filter," Semicond. Sci. Technol. 12; (UK), (1997); pp. 1161–1165.

L. Kasarian, "A New Optical Fiber Multiplexer for Distortion–Free Light Transfer in Multichannel Fiber Optic Sensor Systems," Elsevier; Sensors and Actuators 84; (2000); pp. 250–258.

X. Yan et al., "Electric Field Controlled 2×2 Bypass Exchange Photorefractive Switch," IOP Publishing; (UK) (1998), pp. 383–386.

E. Piener et al., "A Micromachined Vibration Sensor Based on the Control of Power Transmitted Between Optical Fibres," Elsevier; Sensors and Actuators A65; (1998) pp. 23–29.

D. Sun et al., "High Performance Unidirectional Electrooptic Modulator Based On Polymeric Highly Multi–Mode Waveguides,"Elsevier; Optics & Laser Technology 30; (1998); 481–489.

Engin Molva; "Microchip Lasers and Their Applications In Optical Microsystems," Elsevier; Optical Materials 11; (1999); pp. 289–299.

J. Linares et al., "Theory and Design of an Integrated Optical Sensor Based on Planar Waveguiding Lenses," Elsevier; Optics Communications 180; (2000); pp. 29–36.

O. Parriaux et al., "Coupling Gratings as Waveguide Functional Elements," IOP Publishing; Pure Appl. Opt. 5; (1996); pp. 453–469.

E T Enikov et al., "Three–Dimensional Microfabrication for a Multi– Degree of Freedom Capacitive Force Sensor Using Fibre–Chip Coupling" IOP Publishing; (UK); J. Micromechl. Microeng. 10;(2000) pp. 492–497.

J. Holm et al., "Through–Etched Silicon Carriers for Passive Alighnment of Optical Fibers to Surface–Active Optoelectronic Components" Elsevier;Sensors and Actuators 82; (2000) pp. 245–248.

M. Kimura et al., "Vibration Sensor Using Optical–Fiber Catilever with Bulb–Lens" Elsevier; Sensors and Actuators A66; (2000) pp. 178–183.

Y. Mao et al., "Three–Stage Wavelength Converter Based on Cross–Grain Modulation in Semiconductor Optical Amplifiers"Elsevier; Optics Communications 167; (1999) pp. 57–66.

X. Hu et al., "Dynamically Induced Irreversibility: Light Amplification and Quantum Noise Reduction in a V–Type Three–Level System" IOP Publishing; J. Opt. B: Quantum Semiclass. Opt. 2; (UK) (2000); pp. 570–575.

Y. Yim et al., "Lithium Niobate Integrated–Optic Voltage Sensorwith Variable Sensing Ranges" Elsevier; Optics Communications 152; Jul. 1, 1998; pp. 225–228.

C. Lee et al., "Electromagnetic Interference Shilding Efficiency of Polyaniline Mixtures and Multilayer Films" Elsevier; Synthetic Metals 102; (1999) pp. 1346–1349.

Marc Desmulliez, "Optoelectronics–VLSI System Integration Technological Challenges" Elsevier; Materials Science and Engineering B74;(2000) pp. 269–275.

J. Zook et al., "Fiber–optic Vibration Sensor Baed on Frequency Modulation of Light–Excited Oscillators" Elsevier; Sensors and Actuators 83; (2000); pp. 270–276.

M. Reta–Hernandez et al.,"Attenuation of Low Frequency Magnetic Fields Using Active Shielding" Elsevier; Electric Power Systems Research 45; (1998); pp. 57–63.

C. Huang et al., "The EMI Shielding Effectiveness of PC/ABS/Nickel–Coated Carbon–Fibre Composites" Elsevier; European Polymer Journal 36; (2000) pp. 2727–2737.

M. Balucani et al., "Optical Link for Digital/Transmissions Using Porou Silicon Light Emitting Diode" Elsevier; Journal of Non–Crystalline Solids 266–269; (2000) pp. 1238–1240.

D. Egelman et al., "Calcium Dynamics in the Extracellular Space of Mammalian Nerual Tissue" Biophysical Journal; vol. 76; Apr. 1999; pp. 1856–1867.

* cited by examiner

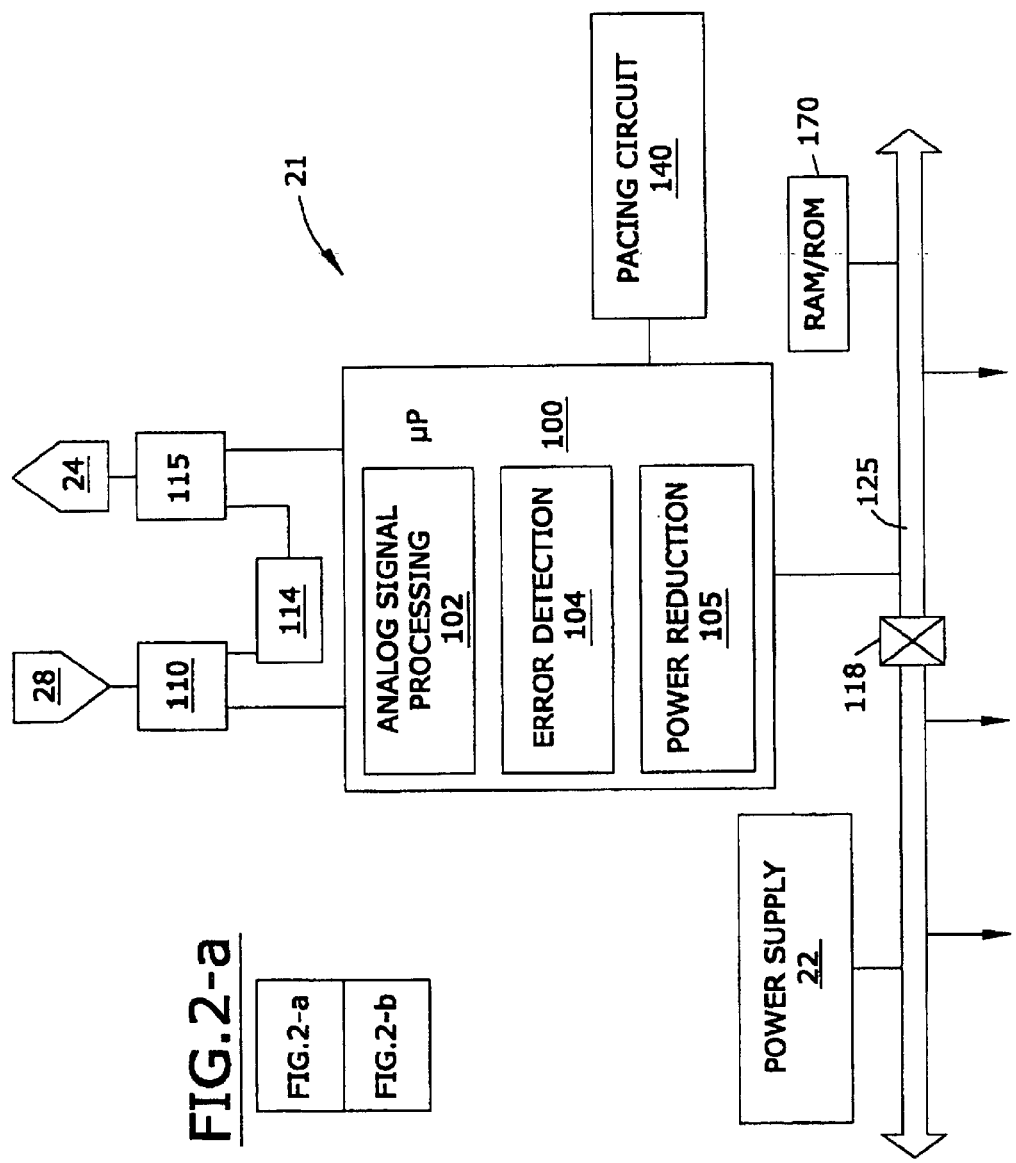

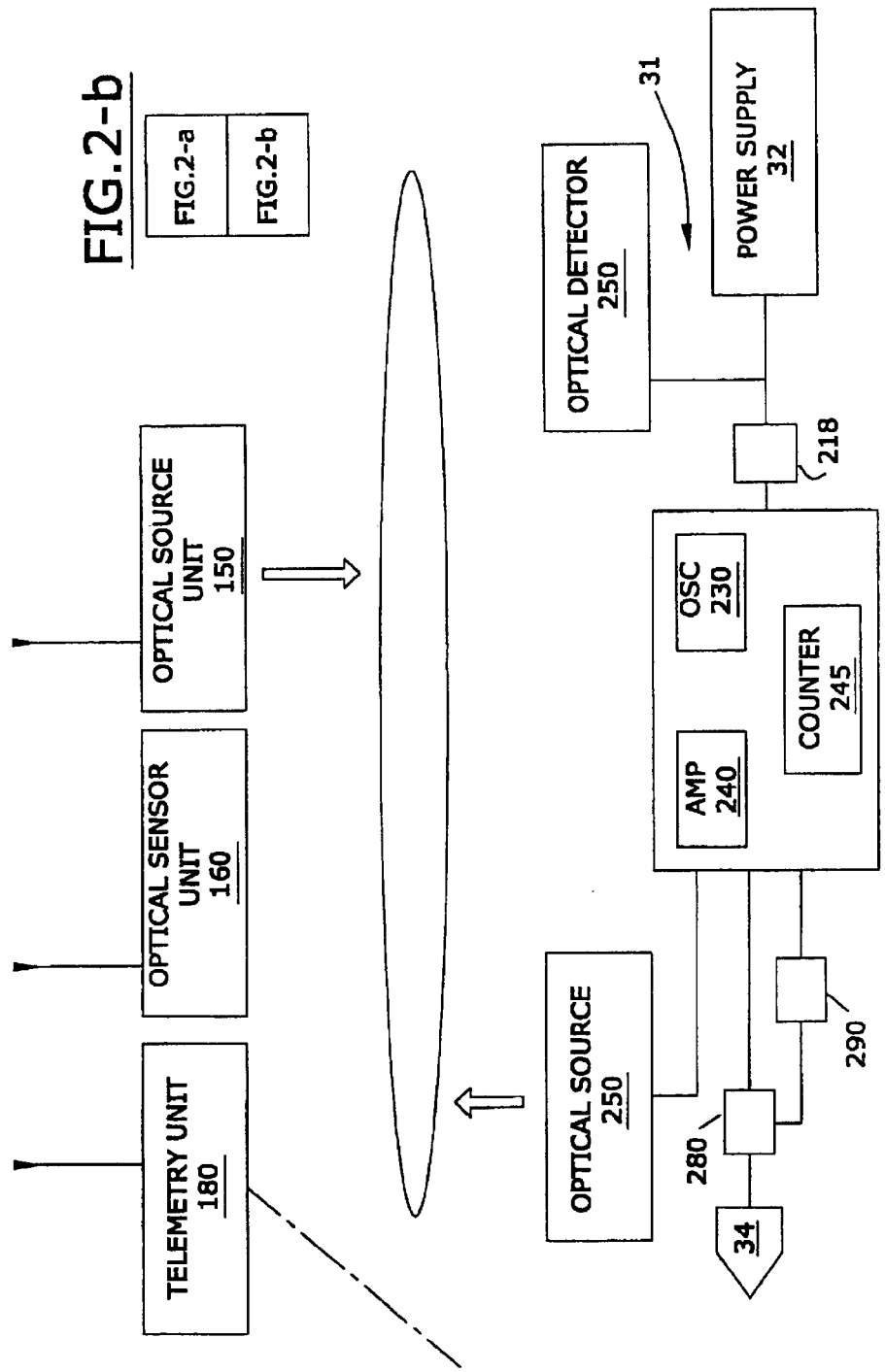

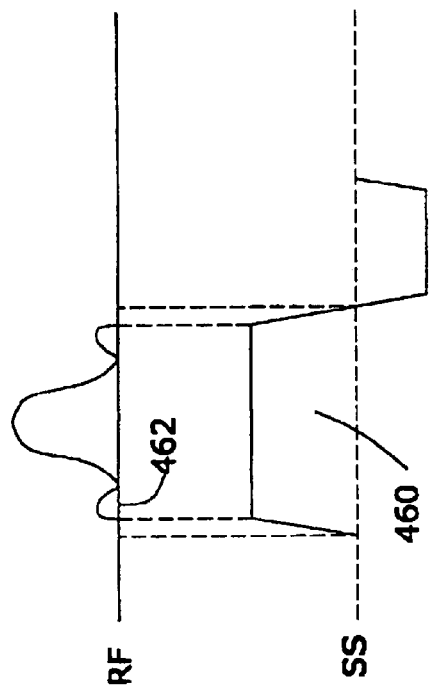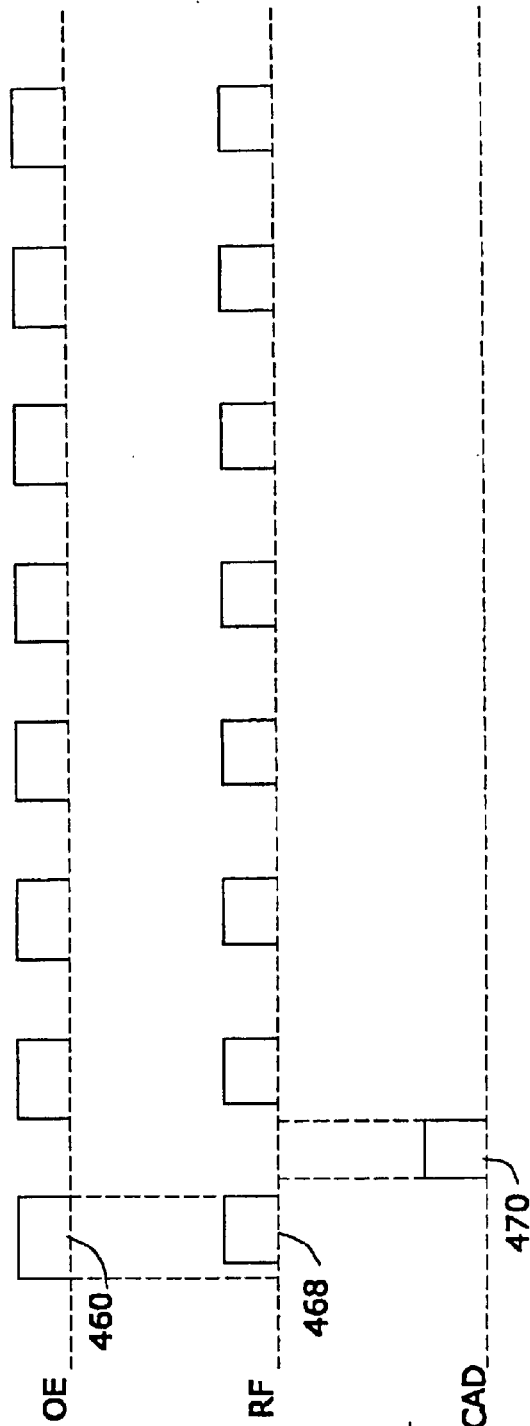

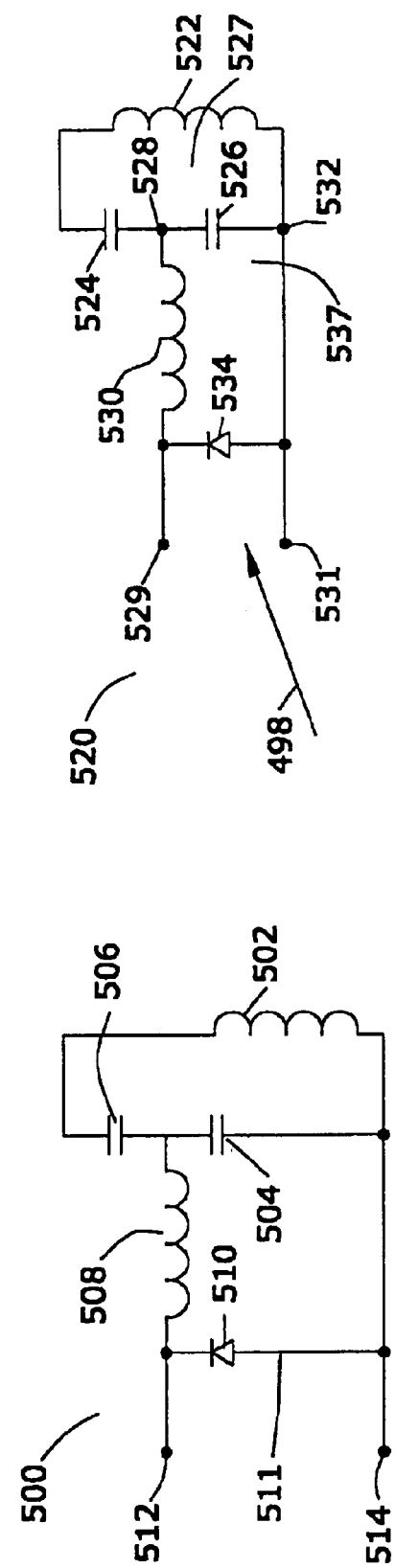

MRI-COMPATIBLE IMPLANTABLE DEVICE

CROSS-REFERENCE TO RELATED PATENT APPLICATION

This application is a continuation-in-part of applicants' copending patent application U.S. Ser. No. 09/839,286, filed on Apr. 20, 2001. Priority for the U.S. Ser. No. 09/839,286 case was based upon provisional patent application U.S. Ser. No. 60/198,631, filed on Apr. 20, 2000.

FIELD OF THE INVENTION

A cardiac assist apparatus with a controller comprised of a parallel resonant frequency circuit activated by energy input.

BACKGROUND OF THE INVENTION

Magnetic resonance imaging (MRI) has been developed as an imaging technique adapted to obtain both images of anatomical features of human patients as well as some aspects of the functional activities of biological tissue. These images have medical diagnostic value in determining the state of the health of the tissue examined.

Thus, e.g., as is disclosed in U.S. Pat. No. 6,144,205 (the entire disclosure of which is hereby incorporated by reference into this specification), in an MRI process a patient is typically aligned to place the portion of his anatomy to be examined in the imaging volume of the MRI apparatus. Such MRI apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $X_3$, respectively). A magnetic field gradient ($\Delta B_z/\Delta x_i$) refers to the variation of the field along the direction parallel to $B_0$ with respect to each of the three principal Cartesian axes, $x_i$. The apparatus also comprises one or more RF (radiofrequency) coils which provide excitation and detection of the NMR signal.

The use of the MRI process with patients who have implanted pacemakers often presents problems. As is known to those skilled in the art, implantable devices (such as implantable pulse generators (IPGs) and cardioverter/defibrillator/pacemakers (CDPs)) are sensitive to a variety of forms of electromagnetic interference (EMI). These devices include sensing and logic systems that respond to low-level signals from the heart. Because the sensing systems and conductive elements of these implantable devices are responsive to changes in local electromagnetic fields, they are vulnerable to external sources of severe electromagnetic noise, and in particular to electromagnetic fields emitted during the magnetic resonance imaging (MRI) procedure. Thus, patients with implantable devices are generally advised not to undergo magnetic resonance imaging (MRI) procedures.

Attempts have been made to protect implantable devices from MRI fields. Thus, for example, U.S. Pat. No. 5,217,010 (to Tsitlik et al.) describes the use of inductive and capacitive filter elements to protect internal circuitry. U.S. Pat. No. 5,968,083 (to Ciciarelli et al.) describes a device adapted to switch between low and high impedance modes of operation in response to EMI insult. U.S. Pat. No. 6,188,926 (to Vock) discloses a control unit for adjusting a cardiac pacing rate of a pacing unit to an interference backup rate when heart activity cannot be sensed due to EMI. The entire disclosure of each of these United States patents is hereby incorporated by reference into this specification.

However, the "solutions" presented by these prior art patents are not entirely adequate. The techniques they describe do not provide a fail-safe system when the protective circuitry or the backup modes of the implantable device fail to protect the implantable device from malfunction due to exposure to electromagnetic fields.

It is an object of this invention to provide a device that will cease furnishing power to a pacemaker at specified intervals while an individual is undergoing an MRI procedure.

It is another object of this invention to provide a means for furnishing power to a pacemaker while protecting it from damage induced by certain radio frequency fields.

SUMMARY OF THE INVENTION

In accordance with this invention, there is provided a cardiac assist device comprising means for connecting said cardiac assist device to a heart, means for furnishing electrical impulses from said cardiac assist device to said heart, means for ceasing the furnishing of said electrical impulses to said heart, means for receiving pulsed radio frequency fields, and means for receiving optical signals. The device contains a control circuit comprised of a parallel resonant frequency circuit activated by energy input.

BRIEF DESCRIPTION OF THE DRAWINGS

The invention will be described by reference to the following drawings, in which like numerals refer to like elements, and in which:

FIG. 2 is a block diagram showing the functional components the implantable device of FIG. 1;

FIG. 6A is a pulse depiction of a standard MRI device;

FIG. 6B is a pulse depiction of the optical emitter of the apparatus of this invention;

FIG. 6C is a timing diagram of pulses produced by MRI device, showing its phase relationship to the energy produced by the optical emitter of FIG. 6B;

FIG. 6D is a pulse energy of input and output of the cardiac assist device of this invention, showing the phase relationships between said input and output;

FIGS. 8A through 8D are schematics of various resonant frequency circuits which can be used in the device of FIG. 1;

DESCRIPTION OF THE PREFERRED EMBODIMENTS

This specification is presented in two parts. The first part of the specification discusses the utilization of a secondary backup cardiac assist device. The second part of this specification discloses a cardiac assist device comprising means for connecting said cardiac assist device to a heart, means for furnishing electrical impulses from said cardiac assist device to said heart, means for ceasing the furnishing of said electrical impulses to said heart, means for receiving pulsed radio frequency fields, means for receiving optical signals; the device contains a control circuit comprised of a parallel resonant frequency circuit activated by optical input.

A Secondary Backup Cardiac Assist Device

In one embodiment of the present invention, there is provided an implantable device that is resistant to electromagnetic interference comprising first and second modular components and an arrangement for communication between the first module and second modules. During a normal operating mode, the first module performs physiologic functions and the second module is deactivated. When electromagnetic interference is detected, the second module, which is resistant to EMI insult, is activated and the first module is deactivated to further protect its components from EMI.

There is also provided, in another embodiment, an implantable device used to monitor and maintain at least one physiologic function, which is capable of operating in the presence of damaging electromagnetic interference. The implantable device includes primary and secondary modules, each independently protected from EMI damage via at least one shielding and/or filtering, and a non-electrical communication device for communicating in at least one direction between the primary and the secondary modules. The primary module, in response to input from electrical sensing leads, activates the secondary module in a failsafe mode. In the failsafe mode, the secondary module carries out a physiologic function upon activation and in the presence of electromagnetic interference.

In an advantageous embodiment, the physiologic function performed by the implantable device is a cardiac assist function, and the implantable device is a cardiac assist device.

Figure 1:
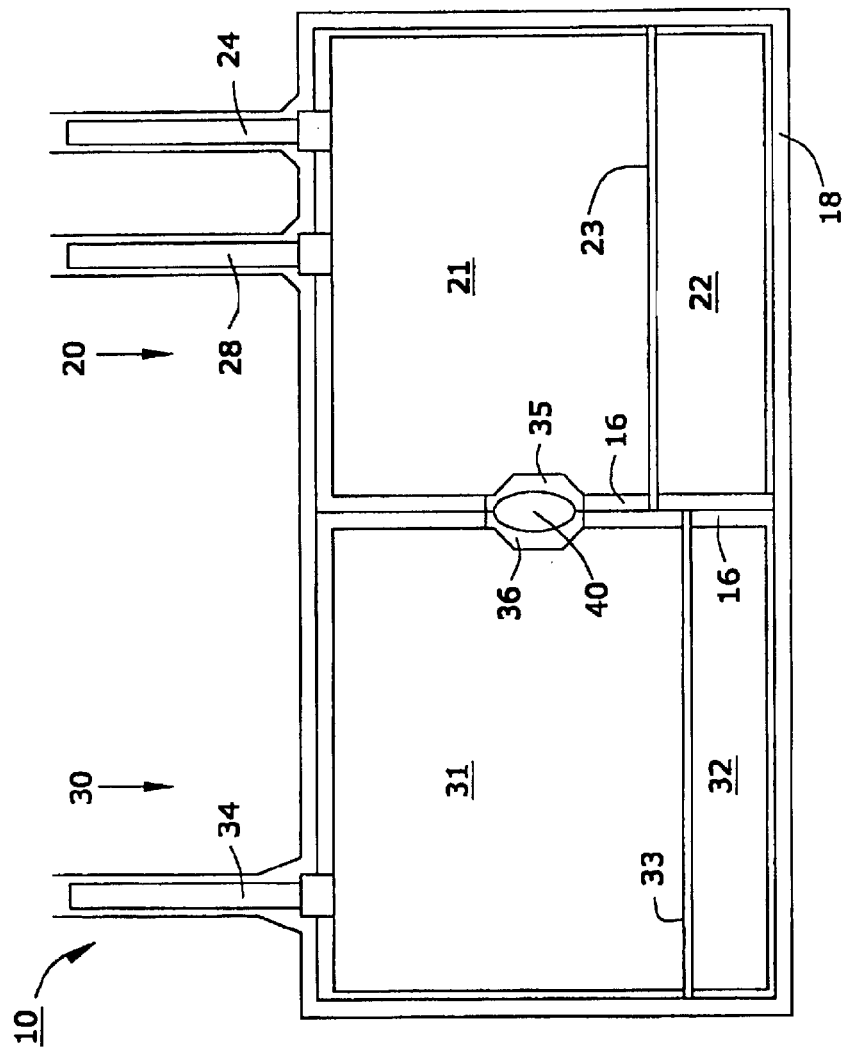
FIG. 1 is sectional view showing a cross-section of one preferred implantable device of the invention.

A cross-section diagram of an embodiment of the implantable device according to one embodiment of the present invention is shown in FIG. 1. The body of the device 10 is shown in rectangular form for illustrative purposes only and may have a rounded shape when implanted in the body to avoid tissue damage due to sharp edges. The body of the implantable device 10 includes two modules, a primary module 20 and a secondary module 30, which are hermetically sealed from each other. As will be described further below, according to an embodiment of the present invention, the primary module is a demand pacemaker (DDD) with PCD functionality. As is known in the art, a demand (DDD) pacemaker denotes an implantable device that paces and senses both atrial and ventrical chambers of the heart and can either trigger or inhibit functions depending on detected parameters. During normal operation, the primary module 20 controls the various pacing, cardioversion and defibrillation operations of the implantable device 10 via electrical pacing lead 24, and detects parameters indicating how the heart is functioning via electrical sensing lead 28. Both the pacing leads and sensing leads are bipolar leads; these leads comprise means for connecting the cardiac assist device to a patient's heart (not shown), and they comprise means for furnishing electrical impulses from the cardiac assist device to the heart.

The primary module 20 includes a circuitry portion 21, which contains signal detection and logic circuitry for performing pacing and analysis functions and a battery portion 22. The battery includes either no magnetic material or non-magnetic materials. It may be, for example, a lithium-iodine battery, or its equivalent in another chemistry, e.g. it may have an anode of lithium or carbon and a cathode of iodine, carbon monofluoride, or of silver vanadium oxide, or sulfur dioxide, $SOCl_2$ or $SO_2 Cl_2$. The circuitry portion 21 is separated from the battery portion by a non-magnetic and non-corrosive layer 23 which, as described below, can be made from titanium or from a carbon-composite material.

The implantable device 10 also includes a secondary module 30, which contains independent circuitry 31, and battery 32 components also separated by a non-magnetic and non-corrosive layer 33. The secondary module 30 is not activated when the primary module 20 operates, but is only switched on when the primary module malfunctions or detects a voltage induced by electromagnetic interference (EMI) that exceeds a certain level, such as, for example, 3 Volts. During such an occurrence, the secondary module 30 acts as a backup VOO pacemaker (ventricle driven, with no ventricle-sensing input nor any ventricular triggering or inhibition), which is ventricle driven, with no ventricle-sensing input nor any ventricular triggering or inhibition. The secondary module 30 sends pacing signals via a unipolar electrical lead 34 to a ventricle chamber of the heart but does not receive any detected input signals. In accordance with its backup function, the secondary module 30 is supplied with power by a separate battery source 32, which is also of a non-magnetic type, such as a lithium-iodine battery.

Both the primary and secondary modules 20, 30 are encased within shieldings 16 that protect their respective circuitry components from external electromagnetic fields. The shieldings 16 can be made from carbon-matrix composites with continuous carbon fiber filler which is particularly effective in EMI shielding, as discussed in "Electromagnetic interference shielding using continuous carbon-fiber carbon-matrix and polymer-matrix composites," Luo, X., and Chung, D. D. L., in Composites: Part B (1999), and also suitable for injection molding to encase circuit components. The thickness of the shielding 16 varies from approximately 1 to 3 millimeters. In addition, the batteries of the primary and secondary modules 22, 32 are also encased in separate shieldings 16 made of similar materials.

An optical window 40, made from glass or ceramic, which may be an infrared-transmissive window, is situated between the respective circuitry portions 21 and 31 of the primary and secondary modules 20, 30. The optical window 40 allows for communication to occur between the primary and secondary modules 20, 30. The window 40 is transparent to a range of frequencies of visible or infrared radiation. The thickness of the window has an optimal range of between 0.3 and 1.0 centimeter. To maintain a hermetic seal between the modules 20, 30, the optical window 40 is bound with brazing to sealing fixtures 35, 36 (also referred to as ferrules) that are welded to the respective modules in a manner that may correspond, for example, to that described in, for example, U.S. Pat. No. 5,902,326 to Lessar et al. The entire disclosure of this United States patent is hereby incorporated by reference into this specification.

To further protect the implantable device 10 from external electromagnetic fields, the entire implantable device 10, including the electrical leads 24, 28, 34, is coated with a non-magnetic, biocompatible layer 18 such as rolled titanium or flexible graphite. Flexible graphite has been shown to be a particularly effective shielding gasket material as discussed, for example, in Flexible Graphite for Gasketing, Adsorption, Electromagnetic Interference Shielding, Vibration Damping, Electrochemical Applications, and Stress Sensing, Chung, D. D. L., Journal of Mat. Eng. and Performance, Vol. 92 (2000), due to its resilience, chemical resistance and shielding properties. Graphite/polymer composites may also serve as layer 18. With both the inner 16 and outer 18 shielding layers in place, only the ends of the electrical leads 24, 28, 34, that are in direct contact with heart tissue remain vulnerable to electromagnetic fields. Since the ends of the leads must be exposed in order to pace the heart or detect electrical impulses, electromagnetic interference can propagate through the ends of the leads to the circuitry of the primary and secondary modules 20, 30. The circuitry described below addresses this problem.

FIG. 2 shows functional components of a dual-module implantable device 10 according to an embodiment of the present invention. As shown, the functional components of the primary module 20 include a power supply (from the battery 22), which supplies power along a main power and device communication bus 125 to the circuitry 21. The circuitry 21 includes a processor 100 coupled to the main bus 125, which can be implemented as a parallel processor, or as a microprocessor adapted to perform analog signal processing functions 102 in addition to error detection 104 and power reduction operations 106. In the analog-processing mode 102, the processor 100 analyzes cardiac signals input from the sensing lead 28 and determines a QRS complex from the various properties of the input signals. The processor 100 determines from the analysis whether a detrimental heart condition exists, and directs a pacing circuit 140 to transmit corrective pulses to ameliorate the condition.

The processor 100 is also configured to detect internal errors or circuitry malfunctions. As will be described further, when such errors are detected, the processor 100 initiates a shut down of the primary module 20 and sends a signal via optical window 40 that instructs module 30 to become activated. Furthermore, to preserve the life of the battery 22 for as long as possible, the processor 100 regulates the application of power to various circuit elements in order to reduce static power consumption, in a manner such as described, for example, in U.S. Pat. No. 5,916,237 to Schu; the entire disclosure of this United States patent is hereby incorporated by reference into this specification. The processor 100 is coupled to a memory unit 170 in which instructions and data are stored.

The primary module circuitry 21 also includes an optical source unit 150 coupled to the main bus 125. Optical source unit 150 can be any source of visible or infrared radiation that does not consume significant amounts of power, such as a light emitting diode (LED). During normal operation of the primary module, the optical source 150, according to various implementations known in the art, turns on and off with a specific well-defined frequency or remains continually on. The optical source unit 150 is arranged in relation to the optical window 40 so that radiation emitted from the source unit 150 penetrates through the optical window 40 into the secondary module 30. Both the processor 100 and the optical source unit 150 are situated downstream from a power-down switch 118.

The primary module circuitry 21 also includes an optical sensor unit 160 similarly placed in relation to the optical window 40, in this case, so that it can receive radiation emitted from sources within the secondary module 30. The optical sensor unit 160 preferably is a low-power photodetector sensitive to infrared or visible radiation of a certain wavelength range, preferably from about 400 to 800 nanometers. The optical sensor unit 160 is coupled to the main bus 125 upstream from the power-down switch 118, so that it remains connected to the power supply 22 via the main bus 125 and therefore remains functional, even when the power-down switch 118 is opened.

Similarly, a telemetry unit 180 is also situated upstream from the power-down switch 118 so it also can function when the power-down switch 118 is opened. The telemetry unit 180 may be, for example, a subcutaneous near-infrared signal transmitter, such as described in U.S. Pat. No. 6,192,261 to Gratton et al., that radiates through body tissues and can communicate with a near-by remote programming device equipped with an infrared receiver, for example, during an examination at a medical facility; the entire disclosure of this United States patent is hereby incorporated by reference into this specification. In another implementation, the telemetry unit may use low-power high-frequency radio signals in the Bluetooth® range to communicate with nearby Bluetooth-enabled network devices. In either case, the telemetry unit 180 can communicate information such as the condition of the heart, the remaining life of the implantable device batteries, and whether the primary module 20 is inoperative.

The processor 100 is coupled to pacing lead 24 and sensing lead 28 via respective comparators 110 and 115. The comparator 110 compares voltage on the input lead 28 with a threshold voltage, set to, for example 3 Volts. If the input voltage exceeds the threshold voltage, the comparator 110 sends a signal to the processor 100. The comparator 115 is reverse biased, so that it compares voltages caused by external fields, rather than the output pulse signal on the pacing lead 24, to the threshold voltage, also set to, for example, 3 Volts. If the external voltage appearing on the pacing lead exceeds the threshold voltage, the comparator 115 sends a signal to the processor 100.

When a voltage exceeds the threshold, this indicates that external EMI fields, which may be caused by an MRI device, are present, and that normal operation of the primary module is to cease. To protect the primary module 20, from excessive voltage signals, a switch (not shown) is thrown to redirect lead signal through capacitive and inductive elements 114, which filter signals on the pacing 24 and sensing 28 leads in a way known in the art before they reach the circuitry 21 of the primary module 20. Upon receiving the threshold signal from either comparators 110 or 115, the processor 100 sends a power-down signal to open the switch 118. Additionally, the processor 100 may send a power-down signal to open the switch 118 in response to detection of internal errors or malfunctions. U.S. Pat. No. 5,653,735 describes, for example, one way by which error detection module 104 can detect malfunctions in primary module 20 not caused by EMI; the entire disclosure of this United States patent is hereby incorporated by reference into this specification.

When the power-down switch 118 is opened, the primary module circuitry components downstream from the switch are disconnected from the power supply 22 and no longer operate. In particular, the primary module 20 stops transmitting pacing pulses to the heart and the optical source unit 150 stops radiating through the optical window 40. As noted above, the telemetry unit 180 and the optical sensor unit 160 of the primary module 20 continue operating. When the optical source unit 150 of the primary module 20 stops emitting radiation, this event is detected by the optical detector 260 of the secondary module 30, which is adapted to detect an absence of radiation of either a certain frequency or for a defined period of time, for example, two seconds. Upon detection, the optical detector 260 transmits a powerup signal to switch 218, which closes and connects the secondary module circuitry 31 to the secondary power supply 32. In this manner, the secondary module 30 is activated when the primary module 20 is deactivated.

Figure 3:
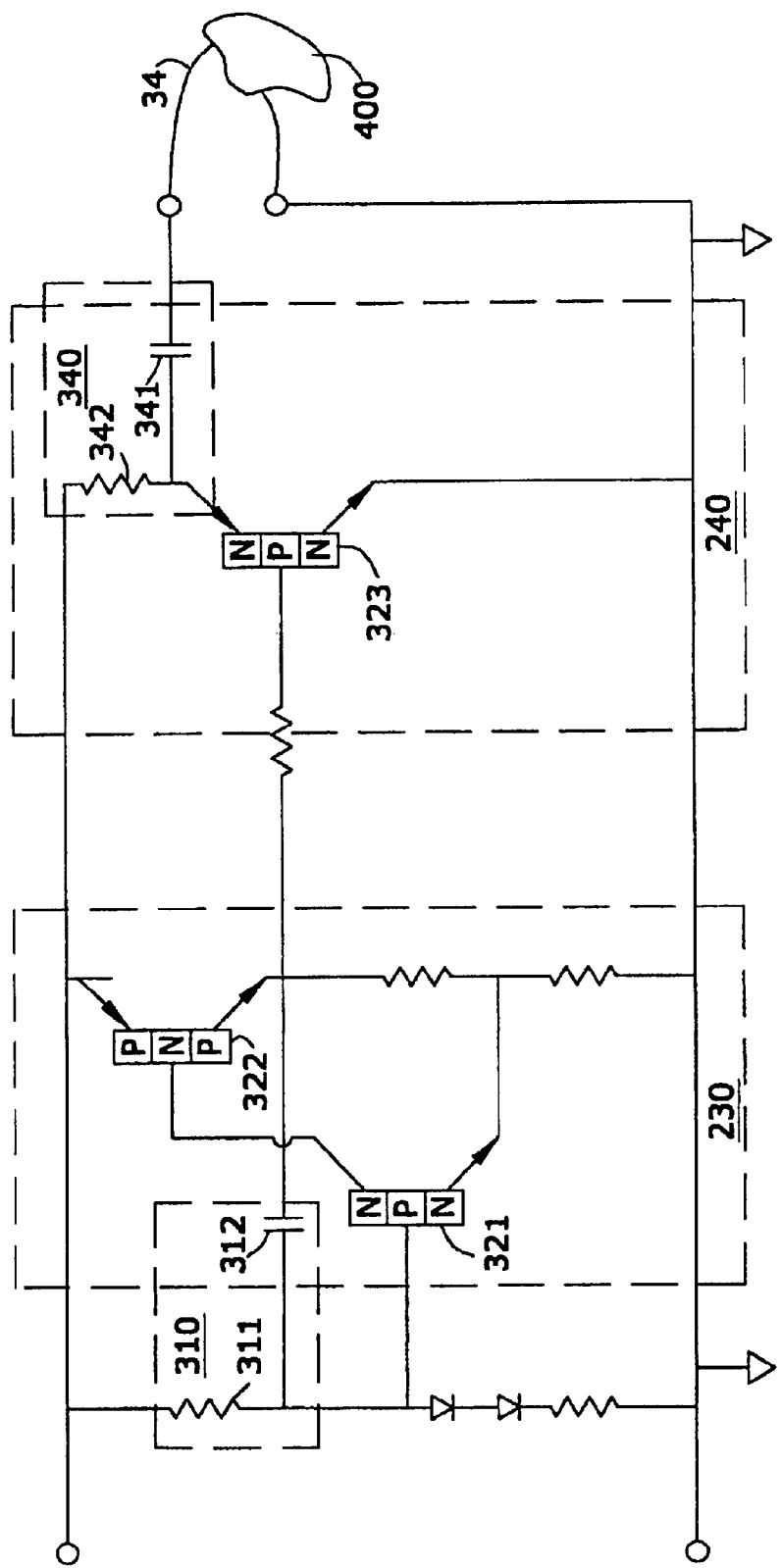
FIG. 3 is a schematic of a robust pacing circuit utilized in the device of FIG. 1.

The secondary module circuitry 31 includes an oscillator stage 230, an amplifier stage 240 and a counter 245. FIG. 3 shows an exploded view of the oscillator 230 and amplifier 240 stages, which are comprised of robust electrical components, such as bipolar transistors, that are not easily disturbed by electromagnetic insult. The oscillator 230 includes bipolar transistors 321 and 322 which are coupled in an emitter feedback arrangement. The RC circuit 310 comprised of resistor 311 and capacitor 312 sets the fixed repetition rate of the oscillator 230. Once the secondary module 30 is turned on, a pulse is produced and sent on to an amplifier stage 240 comprising bipolar transistor 323. A shaping RC circuit 340, comprising capacitor 341 and resistor 342 modifies the shape of a pulse that triggers the ventricle tissues in the heart (shown as 400). This secondary module circuitry 31 generates an electrical pulse that stimulates the heart tissues 52 via a lead 34 extending from the secondary module 30, whereby it produces ventricular contraction at a fixed rate. The return path for the pulse signal is through lead 34 from the body tissues 400 to the secondary module 30. Since the pacing lead 34 can conduct electromagnetic interference, a reverse biased comparator 280 switches the conducting path to capacitive and inductive filtering elements 290 when a threshold voltage is reached. This adds an extra layer of protection to the secondary module circuitry 31.

Because the secondary module 30 only performs basic pacing operations and does not perform diagnostic functions, if the primary module 20 shuts down in response to temporary electromagnetic interference, it is important to reactivate the primary module 20 (and deactivate the secondary module 30) when the implantable device 10 is no longer threatened by the electromagnetic interference. For example, since MRI procedures generally last approximately half an hour, the primary module 20 should only be deactivated for a half an hour plus an additional amount as a tolerance factor, for example.

To keep track of the length of time the secondary module 30 is operating, the secondary module circuitry 31 includes a counter element 245 coupled to the oscillator element 230, that counts oscillator transitions. Once the secondary module is turned on, the counter element 245 increments and can trigger a reset function to turn the primary module 20 back on when it reaches a specific count after a pre-defined length of time.

In one embodiment, the counter 245 triggers an optical source 250 to transmit radiation through the optical window 40 to the primary module 20 in which the radiation is detected by optical sensor unit 160. For example, this radiation may be a single pulse lasting for one second. In response to detection of radiation, the optical sensor unit 160 sends a trigger signal to close the power-down switch 118 and turn the primary module 20 back on. When the processor 100 of the primary module 20 detects that it is connected to the power supply 22, it runs diagnostic tests in a power-on-reset (POR) mode, such as described, for example, in U.S. Pat. No. 6,016,448 to Busacker et al., wherein initial conditions of the heart are determined and stored in memory unit 170; the entire disclosure of this patent is hereby incorporated by reference into this specification. During this mode, the processor 100 also runs internal error checks, so that if the original power-down was caused by internal malfunction, and the cause of the malfunction has not been corrected, the secondary module is not deactivated.

If the internal error checks indicate that the primary module circuitry 21 can support the PCD cardiac assist functions properly, the processor 100 sends a trigger to the pacing unit 140 to begin operation and simultaneously sends a transmission signal to the optical source unit 150, whereupon the optical source unit 150 turns on or begins to pulse according to its pre-set frequency. The optical detector 260 of the secondary unit then detects that the optical source unit 150 of the primary unit is on, and in response, triggers the switch 218 to open, deactivating the secondary module circuitry 31.

Figure 4:
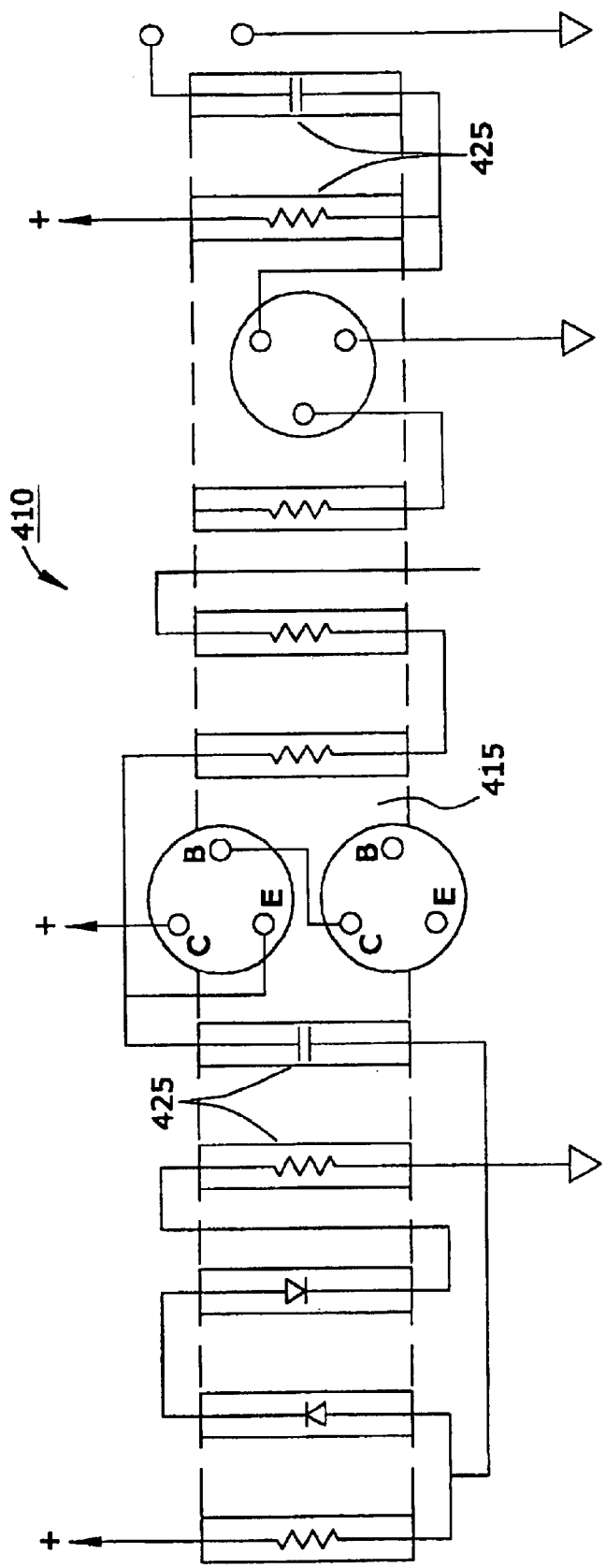
FIG. 4 is schematic illustrating a "cordwood" construction of the pacing circuitry of the device of FIG. 1.

To further improve the EMI resistance of the secondary module 30, the circuitry components 31 may be arranged, according to one embodiment of the secondary module circuitry 31, in a "cordwood" design such as is shown in FIG. 4. As illustrated, in this arrangement all components are laid side by side on a teflon block 415, to avoid adherence, and a thin layer of mixed epoxy is laid onto the circuit components, which are aligned so as to minimize the wiring between the various components which reduces extraneous induced EMI pickup. When the epoxy has cured, the circuit 410 is removed from the teflon block and the components are wired as illustrated in FIG. 4. The resistor and capacitor components 425 are shown hand-wired with very short leads, which reduces electrical pickup signals from an MRI in progress that might disturb the operation of the pacemaker circuitry.

In another embodiment, the secondary module circuitry 31 comprises a custom designed integrated circuit (IC) fabricated, with the active semiconductors, resistors, capacitors and the connecting wires part of the IC. A monolithic IC of this type is described, for example, in U.S. Pat. No. 5,649,956 965 to Pons et al. The entire disclosure of this patent is hereby incorporated by reference into this specification.

Another Embodiment of the Invention Utilizing a Parallel Resonant Circuit

MRI has been developed as an imaging modality used to obtain images of anatomical features of human patients as well as some aspects of the functional activity of biological tissue. The images have medical diagnostic value in determining the state of health of the tissue examined. To obtain images, typically, the patient is aligned to place the portion of the anatomy to be examined in the imaging volume of a MRI apparatus. The apparatus typically comprises a primary magnet for supplying a constant magnetic field ($B_0$) which by convention is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). A magnetic field gradient ($\Delta B_z/\Delta x_i$) refers to the variation of the field along the direction parallel to $B_0$ with respect to each of the three principal Cartesian axes, $x_i$. The apparatus also comprises one or more RF (radio frequency) coils which provide excitation and detection of the NMR signal.

As is known to those skilled in the art of MRI scanner design, there is a requirement to isolate the RF receive coil from the RF transmit coil. One method to accomplish this is the utilization of a parallel resonant circuit tuned to the Larmor frequency of the MRI system. The Larmor frequency of the MRI system is dependent upon the static magnetic field magnitude. The majority of clinical scanners in use today use a 1.5 Tesla superconducting magnet. There are a variety of static magnetic field magnitudes, which are used in research environments and in the future may be utilized clinically. Through the Larmor relationship it is known that $$\omega = \gamma B_0$$

where ω is in radians per second (=2π times the frequency), γ is the gyromagnetic ratio (approximately 42.6 megahertz [MHz] per Tesla for hydrogen) and $B_0$ is the static magnetic field magnitude. The resonant frequency at 1.5 Tesla for hydrogen in clinical scanners is approximately 63.9 megahertz. Therefore, in the range of 0.5 to 14.1 Tesla, the resonant frequency range will be 21.3 megahertz to 651 megahertz. Clinical MRI almost exclusively images utilizing the resonance of hydrogen, therefore the value for γ of 42.6 megahertz per Tesla is standard.

Figure 5:
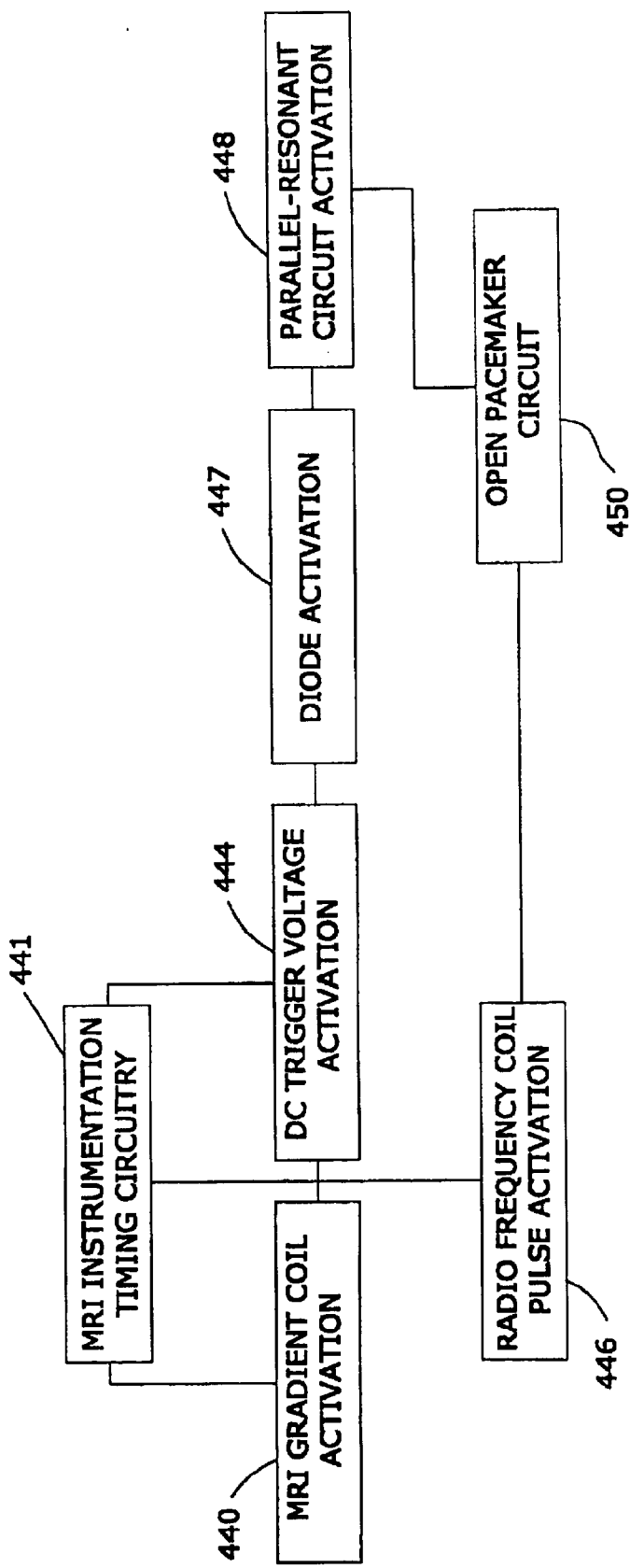
FIG. 5 is a schematic of a preferred process of the invention.

One preferred process of the instant invention is presented in FIG. 5. Referring to FIG. 5, and in step 440 thereof, timing circuitry 441 within the MRI Instrumentation hardware activates the gradient coils of the MRI scanner while substantially simultaneously activating a trigger voltage (see step 444). Thereafter, generally within a period of 3 microseconds, the timing circuitry 441 also activates the transmission of radio frequency coil pulses (see step 446).

One may use timing circuits known to those skilled in the art as MRI timing circuitry 441. Thus, e.g., referring to FIG. 8 of U.S. Pat. No. 4,379,262 ("Nuclear magnetic resonance systems"), there is disclosed a detailed timing and control arrangement 14. The control block shown at element 25 of such FIG. 8 provides the basic control input for the apparatus. This may simply be an operator control panel at which the operator selects the next operation required or may be a microprocessor holding a predetermined control pattern but will generally be a combination of those two. The control 25 supplies instructions to a sequence controller 26. This holds in read only memory a predetermined bit pattern array representing instruction pulses for each of the output lines for each instruction and provides these pulses at timing intervals from timing circuits 27 in response to instructions from 25. Circuits 27 comprise a system clock and appropriate counters and gates. The entire disclosure of this United States patent is hereby incorporated by reference into this specification.

Timing circuits of the type disclosed in U.S. Pat. No. 4,379,262 are well known and are adapted to control any sequence of operations which is known in advance. These circuits can readily be adapted to a chosen examination procedure.

Figure 9:
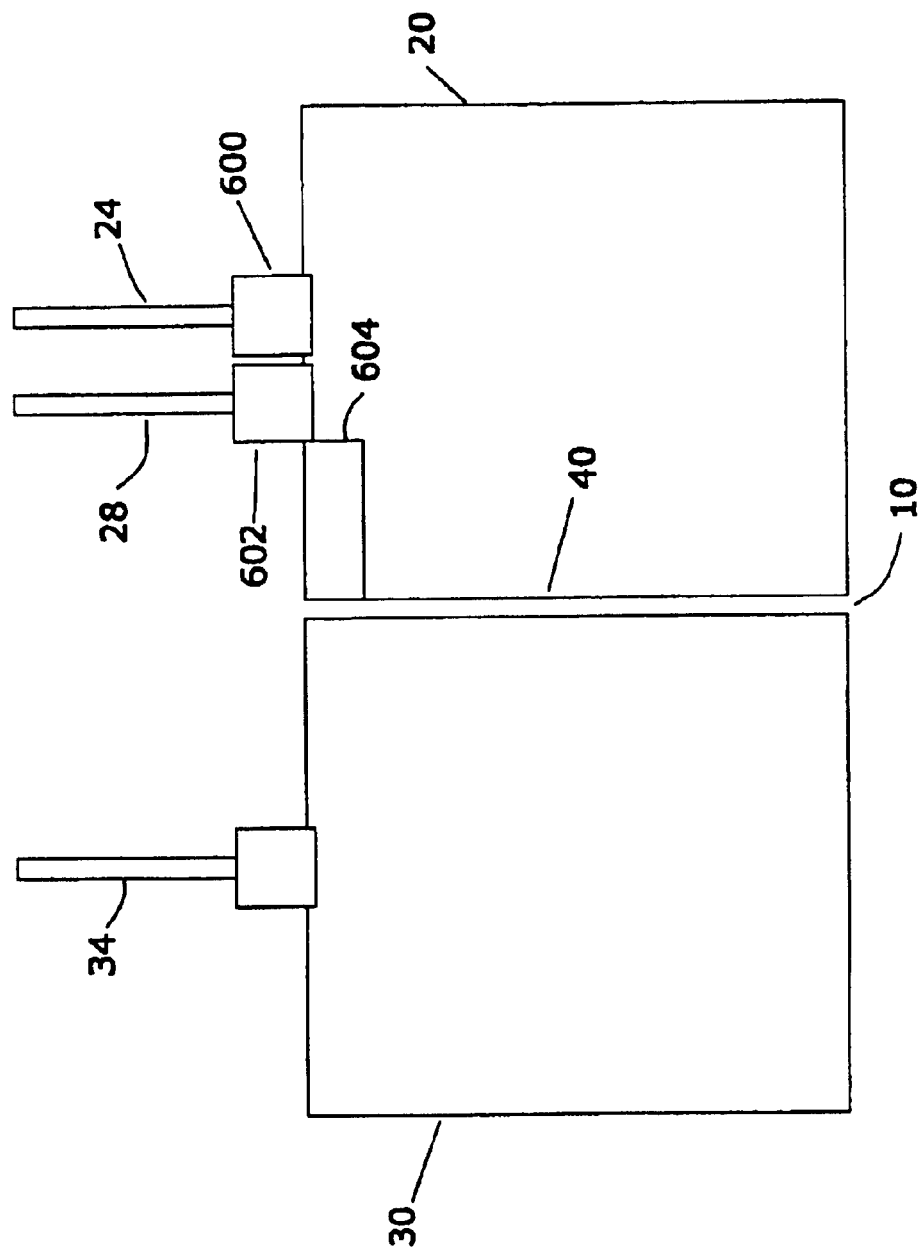
FIG. 9 is a depiction of one preferred implantable device of the invention.

Referring again to U.S. Pat. No. 4,379,262, and to FIG. 9 thereof, it will be seen that the field control 16 gates the field probe output from amplifier 17 with timing signals from 14 and takes a count in counter 28 which is in fact the measured field. Held in a staticiser 29, the measured field is compared in a subtractor 30 with the precalculated field (demand setting) from a store such as a read only memory 31. The consequent error signal is digitised in unit 32 to be applied to coil 12 via a power amplifier, thereby bringing the field to the required value. The entire disclosure of this United States patent is hereby incorporated by reference into specification.

By way of further illustration, suitable MRI instrumentation timing circuitry is disclosed in U.S. Pat. No. 4,333,053 ("Imaging systems"), the entire disclosure of which is hereby incorporated by reference into this specification. Referring to U.S. Pat. No. 4,333,053, and to FIG. 11 thereof, it will be seen that a block diagrammatic circuit for implementing a standard MRI procedure is illustrated. The NMR apparatus (see, e.g., FIG. 1 of U.S. Pat. No. 4,333,053) is indicated as element 40. Element 41, is a timing control unit which cooperates with the NMR apparatus and serves to control the timing of the various operations. It will be appreciated that the operation follows a well defined and predetermined sequence. The times for particular operations are therefore held in stores incorporated in unit 41; and, in response to signals from a system clock 42, timing signals are transmitted to the respective parts of the system. In practice, this, as with many other units, may be incorporated in a digital processor which can control the operation as well as processing the final signals.

Referring again to U.S. Pat. No. 4,333,053, The NMR apparatus 40 is first caused to operate with a GR gradient in the manner previously disclosed, and the resonance signals thus provided are demodulated in demodulators 43 and 44 at frequency $f_0$ from a reference oscillator 45. To preserve phase information, demodulation is into in-phase and quadrature components, the reference for demodulator 44 being shifted by 90° in circuits 46.

Referring again to FIG. 5 of the instant specification, the trigger voltage 444 activated by the timing circuitry 441 will be applied to a specified diode (see step 447), thereby preferably forming a parallel-resonant circuit that is functional only when the resonant condition is met (see FIGS. 8A through 8D for some suitable resonant circuits which utilize such a diode; also see steps 448 and 449 of FIG. 5). As will be apparent, this trigger voltage 444 provides means for furnishing electrical impulses to either an optical emitter (not shown in FIG. 5) and/or for directly activating a diode (not shown).

As is known to those skilled in the art, parallel-resonant circuits have very high impedances at or near the resonant frequency of the circuit and essentially perform as open switches at such resonant frequencies. When the parallel resonant circuit becomes functional (see step 448), it then prevents current at or near the resonant frequency from passing through it. Thus, when this parallel-resonant circuit is interconnected between a cardiac assist device circuit and cardiac leads and is functional, it will effectively open the circuitry of the cardiac assist device, totally inhibiting current induced by the radio frequency fields of the MRI system from flowing to the device or via the leads to the heart (see step 450). Therefore, the functional resonant circuit prevents the occurrence of deleterious effects on the cardiac assist device and the heating of the electrodes placed in the cardiac tissue. Thus, in the device of this application, the parallel resonant circuit which is activated provides means for ceasing the furnishing of electrical impulses from a cardiac assist device to a patient's heart; when alternating currents are supplied which deviate from frequency at which resonance occurs in the parallel resonant circuit, current is allowed to flow to the device, the amount of flow depending upon the deviation from the resonant frequency. Consequently, when the parallel circuit is not activated (at frequencies more or less than the resonant frequency), it acts as a closed switch, and there is provided means for furnishing the electrical impulses to the heart.

As will be apparent to those skilled in the art, the amount of current which will be allowed to flow at frequencies other than the resonant frequency may be adjusted by adjusting the "Q" of the circuit which, in turn, depends upon, e.g., the resistance in the circuit.

When the timing circuitry signals the MRI gradient field pulses and the trigger voltage off, the circuitry of the cardiac assist device is activated because the parallel-resonant circuit ceases to exist. However, since, in this event, the pulsed radio frequency is no longer being produced, there is no danger to the pacemaker circuit and the patient within whom such circuit is disposed.

FIGS. 6A, 6B, 6C, and 6D illustrate one preferred series of phase relationships which preferably are produced by the timing circuit of the MRI device.

Referring to FIG. 6A, the activation of the "slice select" (SS) gradient 460 occurs immediately prior to the application of the radio frequency (RF) pulse 462. The gradient and RF coils activated utilizing the standard pulse sequence in FIG. 6A is of the type magnetic field gradient and RF coils described hereinabove.

A simplified depiction of the timing relationship between the RF coil activation, the triggering of the optical emitter (OE) and the output of the cardiac assist device is shown in FIGS. 6B, 6C and 6D respectively, which illustrate the timing of one embodiment of the present invention. The units of the axis in FIGS. 6A through 6D are relative and can take on many different values. A wide variety of timing sequences are possible depending upon the choice of pulse sequence and type of cardiac assist device. This embodiment of the invention may be applied to any number of time sequences similar to FIGS. 6B, 6C and 6D.

Referring again to FIGS. 6B, 6C, and 6D, the triggering of activation for the optical emitter (OE) 466 precedes the triggering of the activation of the radio frequency (RF) coils of the MRI scanner 468.

Once the radio frequency coils of the MRI scanner are activated, radio frequency fields are generated whose concentration is at a maximum within the core of the coils. These fields interact with and are "received by" all materials with which it contacted. A cardiac assist device within a patient will be contacted and affected by such R.F. fields. The R.F. fields may trigger the cardiac assist device and cause rapid pacing when, in fact, such is not required by the patient. Alternatively, or additionally, the R.F. fields often induce a voltage within the cardiac assist device which is so substantial that it often destroys the device.

As used in the specification, the term "receiving pulsed radio frequency fields" includes any device which is in any manner affected by the pulsed radio frequency fields. Thus, even though the cardiac assist device might not contain a formal antenna for receiving the pulsed radio frequency fields, it still contains means for receiving such pulsed radio frequency fields in that one or more of its components interact with such fields. Without wishing to be bound to any particular theory, applicants believe that the leads of the cardiac assist device often act as antennae.

A multitude of waveforms may be applied for the MRI sequence. There are also a variety of cardiac assist devices (CADs) providing different pulsing and sensing capabilities. The timing description shown in FIG. 6D is only one example of a ventricular VOO pacemaker pulsing waveform. The initiation of any pulse (for example, pulse 470 in FIG. 6D) from the VOO cardiac assist device (CAD) will not occur during a radio frequency pulse derived from the RF transmit coils of the MRI scanner. The duration of this pulse will not overlap or occur during an RF pulse derived from the RF transmit coils of the MRI scanner.

By way of illustration and not limitation, an example of one complex scenario for the sensing and pacing steps is described in U.S. Pat. No. 4,800,883 ("Apparatus for generating multiphasic defibrillation pulse waveform"), the entire disclosure of which is hereby incorporated by reference into this specification.

By way of further illustration, U.S. Pat. No. 6,163,724 ("Microprocessor capture detection circuit and method") discloses means for auto-capture detection in a variety of pacing and sensing modes. Thus, e.g., this patent discloses a software programmable (device means such as a microprocessor) that discriminates between evoked response signals and post-pace polarization signals sensed by an implantable medical device. The polarity of the positive or negative change in voltage in respect of time (or dv/dt) of the waveform incident on the lead electrodes is monitored during a short period of time immediately following a paced event. The patent also discloses that the post-pace polarization signal exhibits a relatively constant polarity during the capture detect window, that the evoked response signal may cause the polarity of post-pace polarization signal to reverse during the capture detect window, that the sign of the post-pace polarization polarity, either positive or negative, is determined by the design of the specific output circuitry. In the device of this patent, the evoked response signal may reverse the polarity of the sensed signal in either case, from positive to negative or from negative to positive, during the time window of interest. In another embodiment of the patent, and when the magnitude of the post-pace polarization is so great that the evoked response does not reverse the polarity of the waveform, discrimination of the evoked response is achieved by noting an acceleration (or increasing magnitude of dv/dt) in the sensed signal or waveform. The entire disclosure of this United States patent is hereby incorporated by reference into this specification.

By way of further illustration, U.S. Pat. No. 6,169,921 ("Autocapture determination for an implantable cardioverter defibrillator") discloses a cardiac pacing/defibrillation system that enhances the ability of a cardiac pacer to automatically detect whether a pacing stimulus results in heart capture or contraction. The cardiac pacing/defibrillation system of this patent includes a pacing circuit that attenuates polarization voltages or "afterpotential" which develop at the heart tissue/electrode interface following the delivery of a stimulus to the heart tissue, which thereby allows the pacing electrodes to be utilized to sense an evoked response to the pacing stimulus. The cardiac pacing/defibrillation system of this patent may utilize the ventricular coil electrode and superior vena cava coil electrode to sense an evoked response, thereby eliminating the necessity for an additional ventricular lead for sensing an evoked response. The device of this patent allows accurate detection of an evoked response of the heart, to thereby determine whether each pacing stimulus results in capture. The entire disclosure of this United States patent is hereby incorporated by reference into this specification.

In step 446 of FIG. 5, a parallel resonant circuit is activated. Some suitable resonant circuits which may be used in the process of this invention are depicted in FIGS. 8A, 8B, 8C, and 8D. In one embodiment of the invention, there is provided a cardiac assist device comprising means for connecting said cardiac assist device to a heart, means for furnishing electrical impulses from said cardiac assist device to said heart, means for ceasing the furnishing of said electrical impulses to said heart, means for receiving pulsed radio frequency fields, and means for receiving optical signals. The device contains a control circuit comprised of a parallel resonant frequency circuit activated by optical input.

Referring again to FIGS. 8A, 8B, 8C, and 8D, radio frequency (RF) energy, of a specified frequency, will cause a resonant circuit to be activated, resulting in a high impedance block of induced current. This high impedance will essentially cause a disconnect between the cardiac leads and the primary and/or secondary module of the device, thereby inhibiting deleterious current to the leads and the modules. When one of the resonant circuits depicted in FIGS. 8A through 8D is not induced, the circuits will simply conduct current between the cardiac assist device and the heart. By choosing the appropriate circuit components, one may choose a "Q" which will provide the desired current flow, or lack thereof, at specified frequencies. At resonance it is a requirement that $$LC = \frac{1}{(2\pi f)^2}$$

where the units of f are in hertz, L are in henries, and C are in farads.

In one embodiment, by the use of a variable resistor (not shown), the "Q" (quality factor) of the parallel resonsant may be varied, thus varying the amount of current which is allowed to flow at specified frequencies off of the resonant frequency.

Figure 8D:
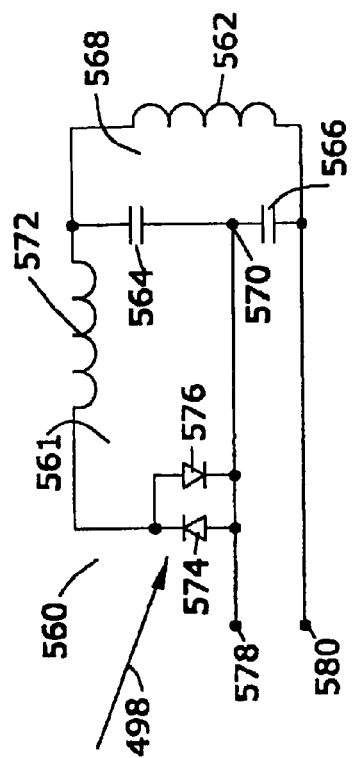

The circuits depicted in FIGS. 8A through 8D are disclosed in U.S. Pat. No. 6,144,205 of Steven Souza et al. The entire disclosure of this United States patent is hereby incorporated by reference into this specification. FIG. 8A corresponds to FIG. 2 of the patent, FIG. 8B corresponds to FIG. 4 of the patent, FIG. 8C corresponds to FIG. 5 of the patent, and FIG. 8D corresponds to FIG. 6 of the patent. This patent claims an antenna assembly for a magnetic resonance imaging system that produces images of a substance, said antenna assembly comprising: a resonant circuit having a first inductance and being tuned to resonate at a Larmor frequency specified herein; a reactive electrical device; a photosensitive first semiconductor switch selectively connecting the reactive electrical device to the resonant circuit, wherein impingement of any optical energy on the photosensitive first semiconductor switch alters connection of the reactive electrical device to the resonant circuit thereby substantially nulling the response of resonant circuit at the Larmor frequency; and a receive coil control coupled to illuminate the photosensitive first semiconductor switch.

The Figures of U.S. Pat. No. 6,144,205 disclose resonant circuits having a first inductance and being tuned to resonate at a Larmor frequency. FIG. 8A depicts one embodiment where a series resonant circuit 500 comprises an inductance 502 with capacitances 504 and 506. Inductance 508, capacitance 504 and PIN diode 510 form a blocking resonant loop coupled through capacitance 504 to the cardiac assist device. As is known to those skilled in the art, PIN diodes are preferably utilized because of their high on/off conductance ratio.

A dc trigger voltage (see step 444 of FIG. 5) is applied to the terminals 512 and 514 from an external source via an electrical lead, such as a lead from a trigger device adapted to produce such voltage when initiated from a separate source, such as the timing circuitry in an MRI scanner. The terminals 512 and 514 also serve as the receiving means of the radio frequency energy of specified frequency of the transmit receiver of the MRI scanner. When the direct current is applied to terminals 512 and 514, and where the bias is such that it produces a forward current through diode 510, the inductance 508 forms a parallel-resonant condition with the capacitance 504. This condition results in the loss of conduction through the entire circuit 500 hence disabling and opening the circuit.

In one preferred embodiment, the direct current 511 applied to PIN diode 508 is applied from an external source via an electrical lead, such a lead from a trigger device adapted to produce such current when initiated by a dc trigger voltage from a separate source, such as the timing circuitry in an MRI scanner. When the direct current 511 is not applied to the PIN diode 510, the circuit is open (disabled).

Figure 8C:
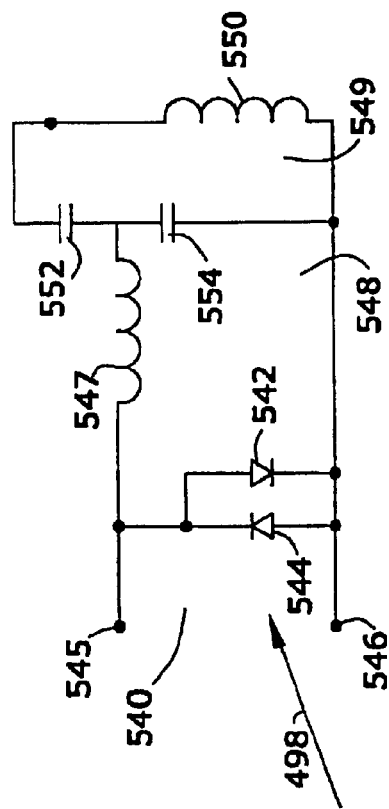

In one preferred embodiment, the diodes 534, 542, 544, 574, and 576 in FIGS. 5B, 8C and 8D will be optically controlled photodiodes. One may use conventional resonant circuits activated by optical switches. Thus, e.g., one may use the parallel resonant circuit switch disclosed in U.S. Pat. No. 5,055,810 ("Ultra-High speed light activated microwave switch/modulation using photoreactive effect"); the entire disclosure of this United States patent is hereby incorporated by reference into this specification. Disclosed in this United States patent is a resonant circuit switch that is controllable via a photodiode. The fabrication of the photodiode illustrated in this patent utilizes the reactance of the photodiode instead of the standard use of the resistance. This results in a drastic increase in the switching speeds of the entire resonant switch.

Referring again to FIG. 8B, the circuit 520 comprises an inductance 522 connected to form a resonant circuit 527 with a pair of series connected capacitances 524 and 526 with an intermediate node 528 between the capacitances. The resonant circuit 527 is tuned to the Larmor frequency of the substance being examined by MRI, (e.g., human tissue). In one embodiment the dc trigger voltage can be linked through an electrical lead to terminal 529 to the intermediate node 528 via an inductor 530 or other reactive electrical device. The other pole of the dc trigger voltage can be linked through an electrical lead to terminal 531 to a node 532 between the second capacitance 532 and inductance 522. A photosensitive semiconductor device, such as a photodiode 534, is connected to the dc trigger voltage without regard to diode polarity. Alternatively, the photosensitive device could comprise a PIN-type photodiode, a phototransistor, a photodarlington transistor pair, a light-activated SCR or a photoFET The device of this invention is comprised of means for receiving an energy input and, in response thereto, for activating the parallel resonant circuit described above. One form of energy which will activate the parallel resonant is photonic energy, and a switching device incorporating such photonic energy will be described in the remainder of this specification. Alternatively, or additionally, one may use other forms of energy to activate the parallel resonant circuit. Thus, for example, one may utilize a direct current voltage supplied by the MRI scanner and/or another apparatus to activate, e.g., a diode (such as, e.g., a pin diode).

Figure 7:
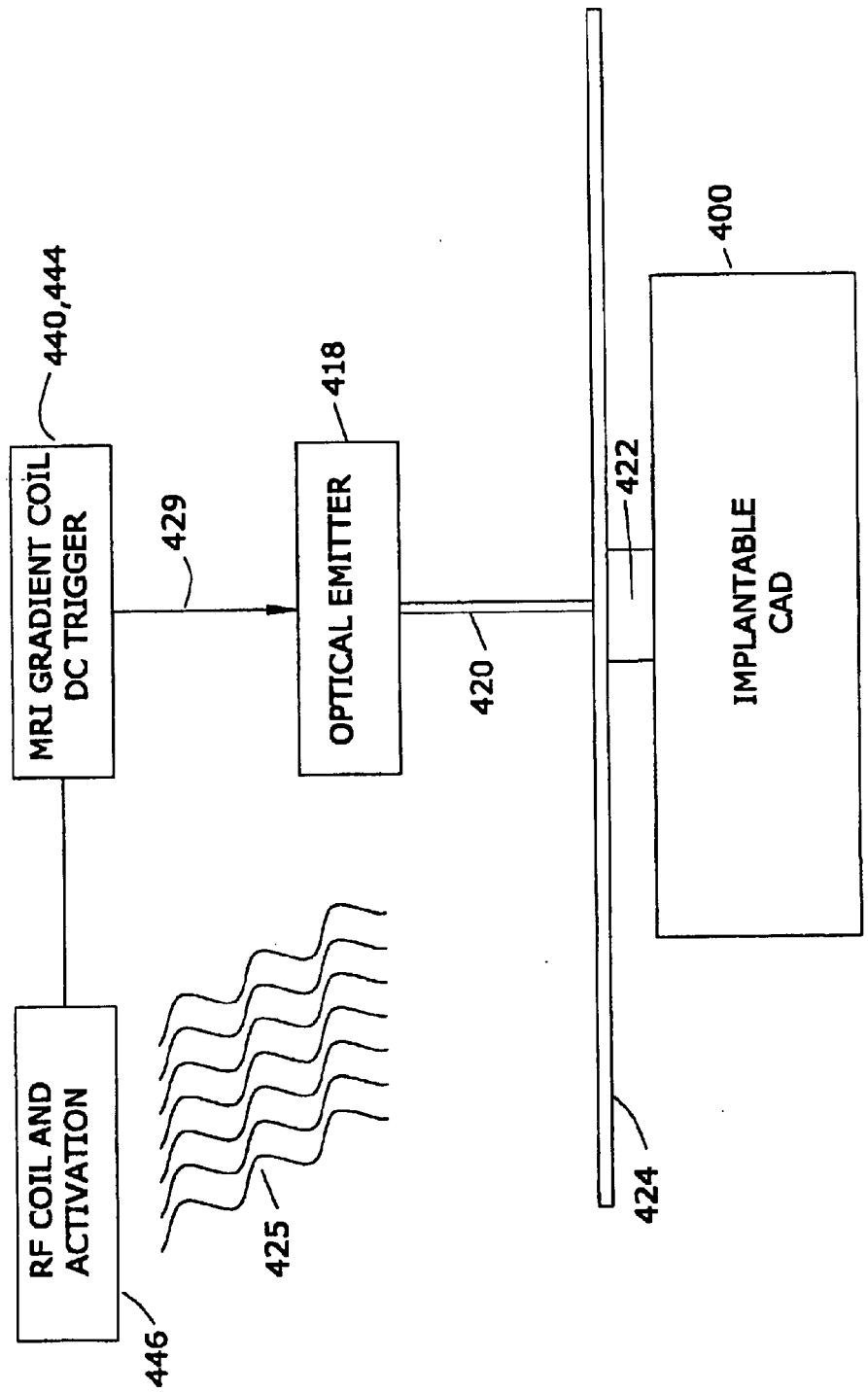
FIG. 7 is a schematic of one preferred embodiment of the present invention.

Referring to both FIGS. 7 and 8B, an in one preferred embodiment of the invention, a transmitted optical signal via a fiber optic cable 520 (see FIG. 8B) may be positioned on or near the skin surface 424 (see FIG. 7) of a patient to illuminate the active surface of photodiode 534. The photodiode 534 may be placed within a feed-through assembly 422, as is known to those skilled in the art of designing and constructing capacitive feedthrough assemblies in cardiac assist devices. One may connect the cardiac leads (not shown) to the cardiac assist device 400.

In one embodiment, optical radiation is transmitted through the skin a patient. In one aspect of this embodiment, one may use near infrared light in the range of from about 700 to about 900 nanometers and, preferably, from about 750 to about 850 nanometers. It is often preferred to use optical radiation of from about 775 to about 825 nanometers; it is known that radiation of about 800 nanometers efficiently is transmitted through the skin of human beings.

As will be apparent, a photodector may be disposed beneath the skin, substantially anywhere in the living organism. It is preferred not to have to transmit the light through highly absorbent body tissue, such as a liver, or through bone. However, subcutaneous placement of the photodetector(s) beneath one or more skin layers is relatively efficient.

Referring again to FIG. 7, when the signal on line 429 indicates that the MRI system gradient coils are active 440/444, the optical emitter 418 responds by producing a light beam which is sent through the optical fiber 420. This light beam illuminates the photodiode 534 in the circuit 520, hereby rendering the photodiode conductive. This causes the blocking loop 537 (see FIG. 8B) formed by the photodiode 534, input inductor 530, and the second capacitance 526 to be parallel resonant at the Larmor frequency. The blocking loop 537 is coupled to the resonant circuit 527. This blocking loop parallel resonance substantially nulls the response of the resonant circuit 527 at the Larmor frequency, thereby preventing current from flowing from the electrical leads to the cardiac assist device 400 during RF transmission of an MRI procedure. During the receive mode, the optical emitter 418 does not produce illumination of the photodiode 534 so that the blocking loop 537 does not form a complete parallel resonant circuit and has no effect on the resonant circuit 527. When resonant at the Larmor frequency, blocking loop 537 also presents a high impedance between the cardiac leads and the resonant circuit 527 electrically isolates the two components during the transmission of the RF pulses. Thus any signal induced in the circuit 520, due to the intense transmit fields, will be attenuated before reaching the electronics of the cardiac assist device 400.

In one embodiment, the device depicted in FIG. 5 of U.S. Pat. No. 6,144,205 may be utilized in the apparatus of this invention. Referring to such FIG. 5, and to embodiment 254, the device of such FIG. 5 is similar to the device of FIG. 4 of the patent but has been modified with the addition of a semiconductor switch 188 in parallel with the photosensitive device 190, but with the opposite polarity (i.e. an anti-parallel connection with photosensitive device 190). In such a configuration, the normal forward current between terminals 191 and 192 through semiconductor switch 188 is opposite that of normal forward current between terminals 191 and 192 through photodiode 190. Semiconductor switch 188 may, for example, be a PIN type diode, transistor, FET or SCR. The current produced by the photodiode or other type of photosensitive device 190, when illuminated, will flow through and partially turn on semiconductor switch 188 thereby reducing the net RF impedance between terminals 191 and 192. This will reduce the on-state impedance in blocking loop 194, increasing the degree to which the parallel resonance of blocking loop 194 nulls the response of resonant circuit 195 comprising inductance 196 and two capacitances 197 and 198. The entire disclosure of this United States patent is hereby incorporated by reference into this specification.

As a variation of the aforementioned embodiment, and referring again to U.S. Pat. No. 6,144,205, the semiconductor switch 188 may also be a photodiode or other type of photosensitive device. In this case, best operation will be obtained if provision is made to adequately illuminate both photosensitive devices 190 and 188 in order to render those devices conductive.

FIG. 6 of U.S. Pat. No. 6,144,205 illustrates an alternative third embodiment 354 of the optical technique for disabling an RF antenna. This embodiment has a parallel resonant blocking loop 201, comprised of photosensitive semiconductor switch 214, inductor 212, and capacitance 204 rather than capacitance 206 corresponding to capacitances 174 and 198 in FIGS. 4 and 5 of such patent, respectively, and optionally semiconductor switch 216. This can be done because there is no need to provide an electrically conducting path to photosensitive semiconductor device 214 as is the case for PIN diode 20 in FIG. 2 of this patent. Device 214 may be connected without regard to diode polarity, and may be a photodiode, a PIN-type photodiode, a phototransistor, a photodarlington transistor pair, a light-activated SCR or a photo-FET. If semiconductor switch 216 is omitted the circuit operation is identical to that of the first embodiment in FIG. 4 of this patent, while offering an additional option for physical placement of the components of blocking loop 201. The circuit of FIG. 6 of this patent offers the further advantage that photosensitive semiconductor switch 214 and inductance 212 are not in the signal path between the resonant circuit 208 and the signal cable 158 connected to terminals 218 and 219, and therefore do not attenuate the received signal in receive mode.

As a variation of the third embodiment of this patent, the modifications of the second embodiment of the patent shown in FIG. 5 thereof (that is, the addition of a semiconductor switch 216 anti-parallel with the photosensitive semiconductor device 214) may be applied to the circuit of FIG. 6 of the patent. This will reduce the on state impedance in blocking loop 201, increasing the degree to which the parallel resonance of blocking loop nulls the response of resonant circuit 208. As a further variation of this third embodiment, the anti-parallel semiconductor switch 216 may also be a photodiode or other type of photosensitive device or any semiconductor activated by photodiode 214.

In another embodiment, a circuit as shown in FIGS. 8A through 8D may be placed within a feedthrough assembly within the path of the leads immediately adjacent to the pacing electrode of the cardiac assist device.

Thus, e.g., one may use the device depicted in U.S. Pat. No. 6,031,710, the entire disclosure of which is hereby incorporated by reference into this specification. This patent discloses a capacitive filter feedthrough assembly and method of making the same for shielding an implantable medical device, such as a pacemaker or a defibrillator, from electromagnetic interference or noise. A ferrule is adapted for mounting onto a conductive device housing by welding, soldering, brazing or gluing, and supports a terminal pin for feedthrough passage to a housing interior. A capacitive filter is mounted at the inboard side of a device housing, with capacitive filter electrode plate sets coupled respectively to the housing and the terminal pin by an electrically conductive combination of adhesive, brazing and soldering. In one embodiment of the invention of this patent, multiple capacitive filters are provided in an array within a common base structure, where each capacitive filter is associated with a respective terminal pin.

Referring again to FIG. 7, and in one embodiment thereof, the cardiac assist device 400 will not shut down when the open circuit is established. An open circuit at the lead will be recognized by the cardiac assist device processor as a specific event defined within ROM 170 (see FIG. 2). The cardiac assist device processor 100 (see FIG. 2) will not respond to this event definition and remain in a static state until the parallel-resonance circuit is triggered off and the closed circuit is reestablished between the cardiac leads 24 and 28 (see FIG. 2) and the cardiac assist device 400. For the embodiment utilizing the parallel-resonant circuit on the secondary module 30 there will be no requirement for signaling from the open circuit due to the fact that there is no sensing capability of the VOO secondary module 30.

Referring again to FIG. 1 and FIGS. 9, in one embodiment of the present invention, the cardiac assist device 10 of this invention will be remotely signaled to open the connection between both the sensing lead 28 and the pacing lead 24 of the device and the primary module 20. A feedthrough assembly 602 and 604 (see FIG. 9) connects leads 24 and 28, respectively, wherein such feedthrough assembly contains the resonant circuit(s) of FIGS. 8A and/or 8B and/or 8C and/or 8D, as described hereinabove.

Figure 10:
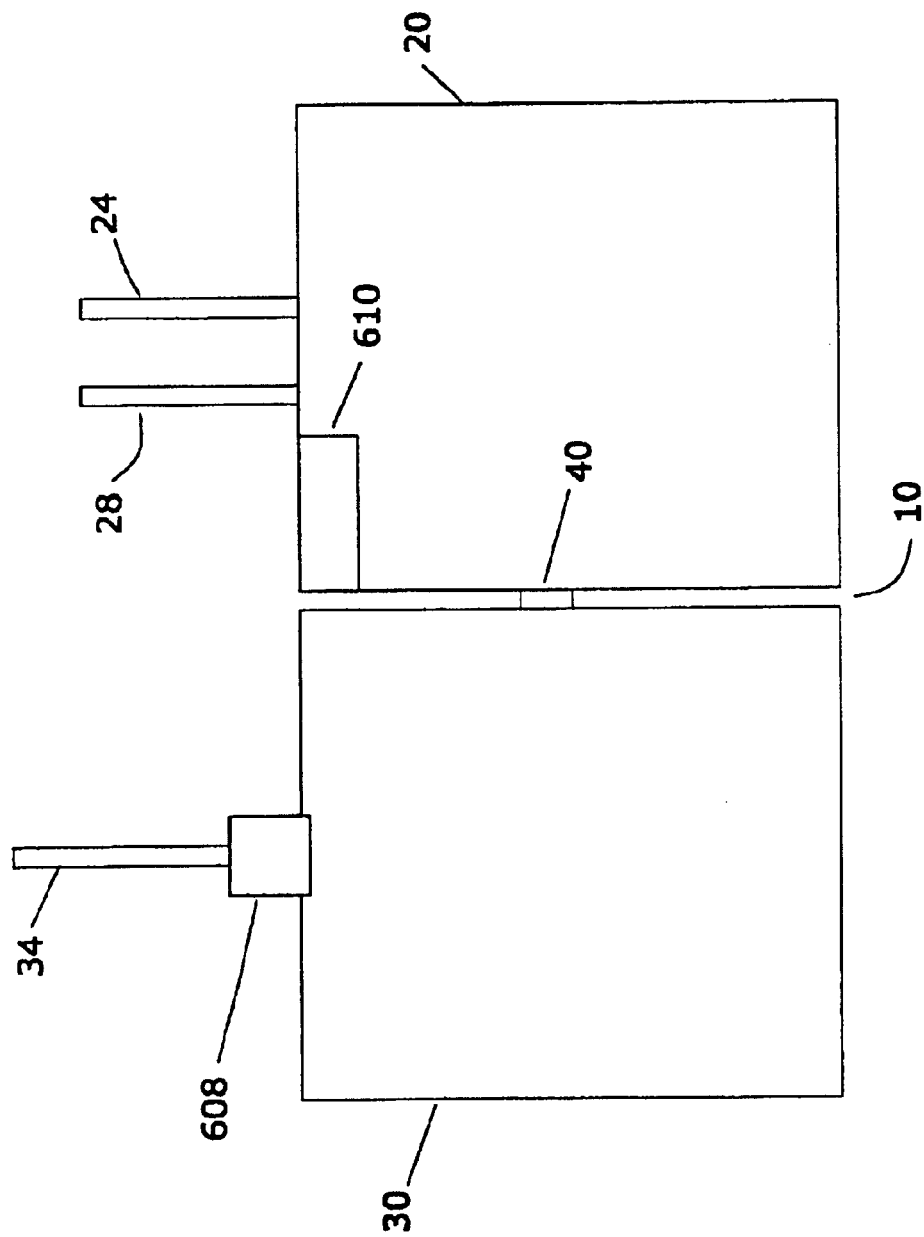
FIG. 10 is a depiction of another preferred implantable device of the invention.

Referring to FIG. 10, the secondary module 30 may also contain the same mechanism remotely signaled to open a connection between the pacing lead 34 and the secondary module 30 via feedthrough assembly 608. In one additional embodiment, an inductor/capacitor/diode (RLC) radio frequency detection circuit for the detection of the frequency specific RF signal is utilized. One of the resonant circuits shown in FIGS. 8A through 8D can be placed at the output end of the sensing lead and at one input into the processor 100. One may use any number of combinations of an RLC resonant circuit to serve the same function as the ones depicted in these Figures. For the purpose of simplicity of representation, additional components described in FIG. 1 have been omitted from FIGS. 9 and 10 but not from the actual specification, unless otherwise noted. The remote signal may be in the form of a radio frequency field (RF) from a magnetic resonance imaging (MRI) scanner.

The use of the resonant circuits of FIGS. 8A through 8D as described in the present invention dictates that the EMI shielding 18 specified in this specification not be utilized on the lead portion of the device specified herein.

In another separate embodiment the secondary module will be omitted and the remote signaling derived from the scanner will influence only a resonant circuit switch from values for the capacitor and inductors within this type of circuit are required such that a high Q value of resonance is acquired within the circuit.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For example, the invention may be used to disable a transmit antenna rather than a receive antenna, and may be used in systems other than MRI systems where similar functionality is desirable. Accordingly, the scope of the invention should be determined from the following claims and not limited by the above disclosure.

We claim:

1. A cardiac assist device comprising means for delivery of electrical current from said cardiac assist device to a heart wherein said means for delivery of electrical current is in electrical communication with said cardiac assist device and said heart, means for transmitting electrical current from said heart to said cardiac assist device wherein said means for transmitting electrical current is in electrical communication with said cardiac assist device and said heart, a control circuit adapted to be responsive to an activation source selected from the group consisting of an optical activation source, a direct current activation source, and combinations thereof and means for ceasing the flow of electrical current through a first circuit wherein said first circuit is selected from the group consisting of said means for delivery of electrical current, said means for transmitting electrical current, and combinations thereof, wherein said means for ceasing the flow of electrical current is controlled by said control circuit, wherein said means for ceasing the flow of electrical current is disposed between said cardiac assist device and said means for delivery of electrical current and said means for transmitting electrical current, and means for receiving pulsed radio frequency fields from an electromagnetic source external to said cardiac assist device, wherein, said means for receiving is selected from the group consisting of said means for delivery of electrical current, said means for transmitting electrical current, said means for ceasing the flow of electrical current, and combinations thereof, wherein said control circuit comprises an optical switch.

2. The cardiac assist device as recited in claim 1, wherein said optical switch comprises a pin type photodiode.

3. The cardiac assist device as recited in claim 2, further comprising an optical fiber connected to said optical switch.

4. The cardiac assist device as recited in claim 1, further comprising said activation source wherein said optical switch is activated by light from said activation source.

5. The cardiac assist device as recited in claim 4, wherein said control circuit is adapted to be disposed within a biological organism.

6. The cardiac assist device as recited in claim 5, wherein said activation source is disposed outside of said biological organism.

7. The cardiac assist device as recited in claim 6, wherein said activation source provides light with a wavelength of from about 750 a to about 850 nanometers.

8. The cardiac assist device as recited in claim 5, wherein said activation source is adapted to be disposed within said biological organism.

9. The cardiac assist device as recited in claim 1, wherein said cardiac assist device is a pacemaker.

10. The cardiac assist device as recited in claim 1, further comprising a magnetic resonance scanner, wherein said electromagnetic source is said magnetic resonance scanner.

11. The cardiac assist device as recited in claim 1, wherein means for ceasing the flow of electrical current is a variable resistor.

12. The cardiac assist device as recited in claim 1, wherein said means for receiving pulsed radio frequency fields is adapted to receive pulsed radio frequency fields in the range from about 30 MHz to about 1000 MHz.

13. A cardiac assist device comprising a pacing lead and a sensing lead wherein said pacing lead and sensing lead are in electrical communication with said cardiac assist device and a heart, further comprising control circuit which is adapted to be responsive to an activation source selected from the group consisting of an optical activation source, a direct current activation source, and combinations thereof, further comprising a resonant circuit wherein said resonant circuit controls the flow of electrical current through a first circuit wherein said first circuit is selected from the group consisting of said pacing lead, said sensing lead, and combinations thereof, wherein said resonant circuit is controlled by said control circuit, wherein said resonant circuit is disposed between said cardiac assist device and said pacing lead and said sensing lead, and an antenna adapted to receive pulsed radio frequency fields from an electromagnetic source external to said cardiac assist device, wherein said antenna is selected from the group consisting of said pacing lead, said sensing lead, said resonant circuit, and combinations thereof.

14. The cardiac assist device as recited in claim 13, wherein said control circuit comprises an optical switch.

15. The cardiac assist device as recited in claim 14, wherein said optical, switch comprises a pin type photodiode.

16. The cardiac assist device as recited in claim 15, further comprising an optical fiber connected to said optical switch.

17. The cardiac assist device as recited in claim 14, further comprising said activation source wherein said optical switch is activated by light from said activation source.

18. The cardiac assist device as recited in claim 17, wherein said control circuit is adapted to be disposed within a biological organism.

19. The cardiac assist device as recited in claim 18, wherein said activation source is disposed outside of said biological organism.

20. The cardiac assist device as recited in claim 19, wherein said activation source provides light with a wavelength of from about 750 to about 850 nanometers.

21. The cardiac assist device as recited in claim 18, wherein said activation source is adapted to be disposed within said biological organism.

22. The cardiac assist device as recited in claim 13, wherein said cardiac assist device is a pacemaker.

23. The cardiac assist device as recited in claim 13, further comprising a magnetic resonance imager, wherein said electromagnetic source is said magnetic resonance imager.

24. The cardiac assist device as recited in claim 13, further comprising means for varying the quality factor of said resonant circuit.

25. The cardiac assist device as recited in claim 24, wherein said means for varying the quality factor of said resonant circuit is a variable resistor.

26. The cardiac assist device as recited in claim 13, wherein said antenna is adapted to receive pulsed radio frequency fields in the range from about 30 MHz to about 1000 MHz.

* * * * *